(12) United States Patent
Schroeder et al.

(10) Patent No.: US 8,262,976 B2
(45) Date of Patent: *Sep. 11, 2012

(54) SOLID STATE DEFORMATION PROCESSING OF CROSSLINKED HIGH MOLECULAR WEIGHT POLYMERIC MATERIALS

(75) Inventors: David Wayne Schroeder, Winona Lake, IN (US); Jordan H. Freedman, Fort Wayne, IN (US); James E. Gunter, Claypool, IN (US); Brian D. Salyer, East Warsaw, IN (US); H. Gene Hawkins, Warsaw, IN (US)

(73) Assignee: Biomet Manufacturing Corp., Warsaw, IN (US)

(*) Notice: Subject to any disclaimer, the term of this patent is extended or adjusted under 35 U.S.C. 154(b) by 134 days.

This patent is subject to a terminal disclaimer.

(21) Appl. No.: 12/471,189

(22) Filed: May 22, 2009

(65) Prior Publication Data

US 2009/0224428 A1     Sep. 10, 2009

Related U.S. Application Data

(60) Division of application No. 11/402,561, filed on Apr. 12, 2006, now Pat. No. 7,547,405, which is a continuation-in-part of application No. 10/963,974, filed on Oct. 13, 2004, now Pat. No. 7,344,672, and a continuation-in-part of application No. 10/963,975, filed on Oct. 13, 2004, now Pat. No. 7,462,318.

(60) Provisional application No. 60/616,811, filed on Oct. 7, 2004.

(51) Int. Cl.
*B29C 51/00* (2006.01)
*B29C 51/02* (2006.01)
*C08J 5/00* (2006.01)

(52) U.S. Cl. .................. 264/319; 264/322; 264/331.11; 264/331.17

(58) Field of Classification Search .................. 264/319, 264/322, 331.11, 331.22, 331.17
See application file for complete search history.

(56) References Cited

U.S. PATENT DOCUMENTS

| 2,948,666 | A | 8/1960 | Lawton |
| 3,362,897 | A | 1/1968 | Lawton |
| 3,563,870 | A | 2/1971 | Tung et al. |

(Continued)

FOREIGN PATENT DOCUMENTS

CA     1 257 745     7/1989

(Continued)

OTHER PUBLICATIONS

"Researchers Get Awards for Orthopaedic Research", The American Academy of Orthopaedic Surgeons, News Release. (Mar. 19, 1998), available at http://www.aaos.org/wordhtml/press/98press/kappa.htm. (4 pages).

(Continued)

*Primary Examiner* — Susan W Berman
(74) *Attorney, Agent, or Firm* — Harness, Dickey

(57) ABSTRACT

Solid-state deformation processing of crosslinked high molecular weight polymers such as UHMWPE, for example by extrusion below the melt transition, produces materials with a desirable combination of physical and chemical properties. Crosslinked bulk materials are heated to a compression deformable temperature, and pressure is applied to change a transverse dimension of the material. After cooling and stress relieving, a treated bulk material is obtained that has enhanced tensile strength in the axial direction orthogonal to the dimension change. In preferred embodiments, medical implant bearing materials are machined from the treated bulk material with the in vivo load bearing axis substantially parallel or coincident with the axial direction of the treated bulk material.

37 Claims, 8 Drawing Sheets

U.S. PATENT DOCUMENTS

| | | | |
|---|---|---|---|
| 3,886,056 A | 5/1975 | Kitamaru et al. |
| 3,956,253 A | 5/1976 | Braun |
| 4,055,862 A | 11/1977 | Farling |
| 4,171,338 A | 10/1979 | Mason |
| 4,224,696 A | 9/1980 | Murray et al. |
| 4,265,959 A | 5/1981 | Sano et al. |
| 4,281,420 A | 8/1981 | Raab |
| 4,348,350 A | 9/1982 | Meier et al. |
| 4,390,666 A | 6/1983 | Moriguchi et al. |
| 4,582,656 A | 4/1986 | Hoffmann |
| 4,586,995 A | 5/1986 | Randall et al. |
| 4,587,163 A | 5/1986 | Zachariades |
| 4,636,340 A | 1/1987 | Itaba et al. |
| 4,655,769 A | 4/1987 | Zachariades |
| 4,668,577 A | 5/1987 | Ohta et al. |
| 4,747,990 A | 5/1988 | Gaussens et al. |
| 4,778,633 A | 10/1988 | Kiang et al. |
| 4,820,466 A | 4/1989 | Zachariades |
| 4,857,247 A | 8/1989 | Raczkowski |
| 4,902,460 A | 2/1990 | Yagi et al. |
| 4,938,913 A | 7/1990 | Ward et al. |
| 5,030,402 A | 7/1991 | Zachariades |
| 5,030,487 A | 7/1991 | Rosenzweig |
| 5,037,928 A | 8/1991 | Li et al. |
| 5,066,755 A | 11/1991 | Lemstra |
| 5,096,654 A | 3/1992 | Craggs et al. |
| 5,130,376 A | 7/1992 | Shih |
| 5,160,464 A | 11/1992 | Ward et al. |
| 5,169,589 A | 12/1992 | Francoeur et al. |
| 5,200,129 A | 4/1993 | Kobayashi et al. |
| 5,200,439 A | 4/1993 | Asanuma |
| 5,204,045 A | 4/1993 | Courval et al. |
| 5,210,130 A | 5/1993 | Howard, Jr. |
| 5,234,652 A | 8/1993 | Woodhams et al. |
| 5,266,246 A | 11/1993 | Johnson et al. |
| 5,276,079 A | 1/1994 | Duan et al. |
| 5,358,529 A | 10/1994 | Davidson |
| 5,405,393 A | 4/1995 | Falkenström |
| 5,407,623 A | 4/1995 | Zachariades et al. |
| 5,414,049 A | 5/1995 | Sun et al. |
| 5,428,079 A | 6/1995 | Bastiaansen et al. |
| 5,439,949 A | 8/1995 | Lucas et al. |
| 5,449,745 A | 9/1995 | Sun et al. |
| 5,466,530 A | 11/1995 | England et al. |
| 5,478,906 A | 12/1995 | Howard, Jr. |
| 5,505,900 A | 4/1996 | Suwanda et al. |
| 5,508,319 A | 4/1996 | DeNicola, Jr. et al. |
| 5,543,471 A | 8/1996 | Sun et al. |
| 5,552,104 A | 9/1996 | DeNicola, Jr. et al. |
| 5,577,368 A | 11/1996 | Hamilton et al. |
| 5,650,485 A | 7/1997 | Sun et al. |
| 5,684,124 A | 11/1997 | Howard, Jr. et al. |
| 5,709,020 A | 1/1998 | Pienkowski et al. |
| 5,728,748 A | 3/1998 | Sun et al. |
| 5,824,411 A | 10/1998 | Shalaby et al. |
| 5,827,904 A | 10/1998 | Hahn |
| 5,830,396 A | 11/1998 | Higgins et al. |
| 5,879,400 A | 3/1999 | Merrill et al. |
| 6,017,975 A | 1/2000 | Saum et al. |
| 6,048,480 A | 4/2000 | Doyle |
| 6,051,487 A | 4/2000 | Gardner et al. |
| 6,143,232 A | 11/2000 | Rohr |
| 6,146,426 A | 11/2000 | Doyle |
| 6,165,220 A | 12/2000 | McKellop et al. |
| 6,168,626 B1 | 1/2001 | Hyon et al. |
| 6,174,934 B1 | 1/2001 | Sun et al. |
| 6,184,265 B1 | 2/2001 | Hamilton et al. |
| 6,228,900 B1 | 5/2001 | Shen et al. |
| 6,242,507 B1 | 6/2001 | Saum et al. |
| 6,245,276 B1 | 6/2001 | McNulty et al. |
| 6,281,264 B1 | 8/2001 | Salovey et al. |
| 6,316,158 B1 | 11/2001 | Saum et al. |
| 6,355,215 B1 | 3/2002 | Poggie et al. |
| 6,365,089 B1 | 4/2002 | Krebs et al. |
| 6,372,814 B1 | 4/2002 | Sun et al. |
| 6,395,799 B1 | 5/2002 | Johnson |
| 6,432,349 B1 | 8/2002 | Pletcher et al. |
| 6,458,727 B1 | 10/2002 | Jones et al. |
| 6,464,926 B1 | 10/2002 | Merrill et al. |
| 6,494,917 B1 | 12/2002 | McKellop et al. |
| 6,503,439 B1 | 1/2003 | Burstein |
| 6,547,828 B2 | 4/2003 | Scott et al. |
| 6,562,540 B2 | 5/2003 | Saum et al. |
| 6,641,617 B1 | 11/2003 | Merrill et al. |
| 6,664,308 B2 | 12/2003 | Sun et al. |
| 6,686,437 B2 | 2/2004 | Buchman et al. |
| 6,692,679 B1 | 2/2004 | McNulty et al. |
| 6,709,464 B2 | 3/2004 | Scott et al. |
| 6,726,727 B2 | 4/2004 | Scott et al. |
| 6,786,933 B2 | 9/2004 | Merrill et al. |
| 6,800,670 B2 | 10/2004 | Shen et al. |
| 6,818,020 B2 | 11/2004 | Sun et al. |
| 6,818,172 B2 | 11/2004 | King et al. |
| 6,852,772 B2 | 2/2005 | Muratoglu et al. |
| 6,905,511 B2 | 6/2005 | Wang et al. |
| 7,268,039 B2 | 9/2007 | Fishburn et al. |
| 7,344,672 B2 | 3/2008 | Schroeder et al. |
| 7,431,874 B2 | 10/2008 | Muratoglu et al. |
| 7,462,318 B2 | 12/2008 | Schroeder et al. |
| 7,498,365 B2 | 3/2009 | Muratoglu et al. |
| 7,517,919 B2 | 4/2009 | Wang et al. |
| 7,547,405 B2 | 6/2009 | Schroeder et al. |
| 7,635,725 B2 | 12/2009 | Bellare et al. |
| 2001/0049401 A1 | 12/2001 | Salovey et al. |
| 2002/0007219 A1 | 1/2002 | Merrill et al. |
| 2002/0037944 A1 | 3/2002 | Shen et al. |
| 2002/0125614 A1 | 9/2002 | King et al. |
| 2002/0156536 A1 | 10/2002 | Harris et al. |
| 2003/0013781 A1 | 1/2003 | Merrill et al. |
| 2003/0045603 A1 | 3/2003 | Salovey et al. |
| 2003/0105182 A1 | 6/2003 | Merrill et al. |
| 2003/0119935 A1 | 6/2003 | Merrill et al. |
| 2003/0125513 A1 | 7/2003 | King |
| 2003/0137081 A1 | 7/2003 | Pitkanen |
| 2003/0139555 A1 | 7/2003 | Hubbard et al. |
| 2003/0158287 A1 | 8/2003 | Salovey et al. |
| 2003/0208278 A1 | 11/2003 | Richard |
| 2003/0212161 A1 | 11/2003 | McKellop et al. |
| 2003/0229155 A1 | 12/2003 | Wang et al. |
| 2004/0132856 A1 | 7/2004 | Merrill et al. |
| 2004/0208841 A1 | 10/2004 | Salovey et al. |
| 2004/0266902 A1 | 12/2004 | Shen et al. |
| 2005/0006821 A1 | 1/2005 | Merrill et al. |
| 2005/0010288 A1 | 1/2005 | Merrill et al. |
| 2005/0043431 A1 | 2/2005 | Wang et al. |
| 2005/0043815 A1 | 2/2005 | King et al. |
| 2005/0048096 A1 | 3/2005 | Shen et al. |
| 2005/0056971 A1 | 3/2005 | Merrill et al. |
| 2005/0059750 A1 | 3/2005 | Sun et al. |
| 2005/0069696 A1 | 3/2005 | King et al. |
| 2005/0096749 A1 | 5/2005 | Merrill et al. |
| 2005/0194723 A1 | 9/2005 | Muratoglu et al. |
| 2006/0264541 A1 | 11/2006 | Lederer et al. |
| 2007/0114702 A1 | 5/2007 | Muratoglu et al. |
| 2007/0265369 A1 | 11/2007 | Muratoglu et al. |
| 2007/0267030 A1 | 11/2007 | Muratoglu et al. |
| 2007/0275030 A1 | 11/2007 | Muratoglu et al. |
| 2008/0067724 A1 | 3/2008 | Muratoglu et al. |
| 2008/0090934 A1 | 4/2008 | Muratoglu et al. |
| 2008/0119582 A1 | 5/2008 | Muratoglu et al. |
| 2008/0140196 A1 | 6/2008 | Schroeder et al. |
| 2008/0214692 A1 | 9/2008 | Muratoglu et al. |
| 2008/0215142 A1 | 9/2008 | Muratoglu et al. |
| 2008/0274161 A1 | 11/2008 | Muratoglu et al. |
| 2009/0054545 A1 | 2/2009 | Muratoglu et al. |
| 2009/0082546 A1 | 3/2009 | Schroeder et al. |

FOREIGN PATENT DOCUMENTS

| | | |
|---|---|---|
| DE | 199 14 571 | 1/2001 |
| EP | 0 729 981 B1 | 3/2002 |
| EP | 1 334 993 | 8/2003 |
| GB | 1281956 | 7/1972 |
| JP | 52-6761 | 7/1975 |
| JP | 57-211347 | 12/1982 |
| JP | 62216723 | 9/1987 |
| JP | 62-243634 | 10/1987 |
| JP | 02-175137 | 7/1990 |

| | | |
|---|---|---|
| JP | 04-198201 | 7/1992 |
| JP | 05-507748 | 11/1993 |
| JP | 91 022222 | 5/1997 |
| JP | 09141729 | 6/1997 |
| JP | 10166468 | 6/1998 |
| JP | 11060791 | 3/1999 |
| JP | 11077778 | 3/1999 |
| WO | WO 93/10953 | 6/1993 |
| WO | WO 95/06148 | 3/1995 |
| WO | WO 98/01085 | 1/1998 |
| WO | WO 98/14223 | 4/1998 |
| WO | WO 03/049930 | 6/2003 |

OTHER PUBLICATIONS

"Researchers to Get Kappa Delta Awards for Achievements" The American Academy of Orthopaedic Surgeons, Academy News. (Mar. 19, 1998), available at http://www.aaos.org/wordhtml/98news/kappa.htm. (3 pages).

Appleby et al. "Post-Gamma Irradiation Cross-linking of Polyethylene Tape by Acetylene Treatment" Journal of Materials Science. vol. 29 (1994) p. 227-231.

Appleby et al. "Property Modification of Polyethylene Tapes by Acetylene-Sensitized Gamma Irradiation" Journal of Materials Science. vol. 29 (1994) p. 151-156.

Bhateja et al. "Radiation-Induced Crystallinity Changes in Polyethylene Blends" Journal of Materials Science. vol. 20 (1985) p. 2839-2845.

Bhateja, S. "Radiation-Induced Crystallinity Changes in Linear Polyethylene" Journal of Polymer Science: Polymer Physics Edition. vol. 21 (1983) p. 523-536.

Bhateja, S. "Radiation-Induced Crystallinity Changes in Linear Polyethylene: Influence of Aging" Journal of Applied Polymer Science. vol. 28 (1983) p. 861-872.

Bhateja, S. "Radiation-Induced Crystallinity Changes in Pressure-Crystallized Ultrahigh Molecular Weight Polyethylene" J. Macromol. Sci. Phys. B22(1) (1983) p. 159-168.

Bowman, J. "The Processing and Properties of γ-Irradiated HDPE Granules" Intern. Polymer Processing III. (1988) p. 211-220.

Chen et al. "Radiation-Induced Crosslinking: II. Effect on the Crystalline and Amorphous Densities of Polyethylene" Colloid Polym Sci. vol. 269 (1991) p. 469-476.

Chen et al. "Radiation-Induced Crosslinking: III. Effect on the Crystalline and Amorphous Density Fluctuations of Polyethylene" Colloid Polym Sci. vol. 269 (1991) p. 353-363.

Choudhury et al. "The Effects of Irradiation and Ageing on the Abrasive Wear Resistance of Ultra High Molecular Weight Polyethylene" Wear Elsevier Science. vol. 203-204 (1997) p. 335-340.

Chu et al. "Some Structures and Properties of Very High Molecular Weight Linear Polyethylene" Bull. Inst. Chem. Res. vol. 47, No. 3 (1969) p. 209-221.

Collier et al. "Polyethylene: The Past, Present and Future" The American Academy of Orthopaedic Surgeons, 1999 Annual Meeting Scientific Program, available at http://www.aaos.org/wordhtml/anmeet99/sciprog/g.htm. (20 pages).

Crugnola et al., Ultrahigh Molecular Weight Polyethylene as Used in Articular Prostheses (A Molecular Weight Distribution Study), J. of App. Polymer Science, vol. 20, (1976) p. 809-812.

Dharmastiti et al. "The Wear of Oriented UHMWPE Under Isotropically Rough and Scratched Counterface Test Conditions" Bio-Medical Materials and Engineering. vol. 11 (2001) p. 241-256.

Dijkstra et al. "Cross-linking of Ultra-high Molecular Weight Polyethylene in the Melt by Means of Electron Beam Irradiation" Polymer. vol. 30 (May 1989) p. 866-873.

Dole et al. "Crystallinity and Crosslinking Efficiency in the Irradiation of Polyethylene" Radiat. Phys. Chem. vol. 14 (1979) p. 711-720.

du Plessis et al. "The Improvement of Polyethylene Prostheses Through Radiation Crosslinking" Radiat. Phys. Chem. vol. 9 (1977) p. 647-652.

Ellis et al., The Use of Ultrahigh Molecular Weight Polyethylene in Articular Prostheses—II. Effects of Fabrication and Gamma Sterilization on Polymer Characteristics, Coatings and Plastics Preprints, vol. 37, No. 2, American Chemical Society, (1977) p. 280-284.

Ellwanger et al. "Very High Pressure Molding of Ultra High Molecular Weight Polyethylene (UHMWPE)" ANTEC. (1987) p. 572-574.

Gallinaro, Clinical Results of Crosslinked UHMWPE, Trans. UHMWPE for arthroplasty: Degradation, stabilization, and crosslinking (2005), p. 140-147.

Gauvin et al., "Investigation of the Radio Frequency Heating Process for UHMWPE" ANTEC. (1987) p. 575-578.

Greenwald et al., New Polys for Old: Contribution or Caveat?, American Academy of Orthopaedic Surgeons, 69th Annual Meeting (Feb. 13-17, 2002) (6 pages).

Handlos, V. "Enhanced Crosslinking of Polyethylene" Radiat. Phys. Chem. vol. 14 (1979) p. 721-728.

Howmedica, Material Properties, Product Quality Control, and Their Relation to UHMWPE Performance, Part Two of a Series on Ultra-High Molecular Weight Polyethylene, (1994) p. 1-20.

Howmedica, Overview and Fundamentals of UHMWPE, Part One of a Series on Ultra-High Molecular Weight Polyethylene, (1994) p. 1-8.

Jahan et al. "Combined Chemical and Mechanical Effects on Free Radicals in UHMWPE Joints During Implantation" Journal of Biomedical Materials Research. vol. 25 (1991) p. 1005-1017.

Jones et al., Effect of γ Irradiation on the Friction and Wear of Ultrahigh Molecular weight Polyethylene, Wear, vol. 70, (1981) p. 77-92.

Josefsson et al. "Molecular Orientation of Crosslinked Polyethylene" Annual Technical Conference—Society of Plastics Engineers, 58th vol. 2 (2000) p. 1725-1729.

Kang et al. "The Radiation Chemistry of Polyethylene IX, Temperaure Coefficient of Cross-Linking and Other Effects" Journal of the American Chemical Society. vol. 89:9 (1967) p. 1980-1986.

Kanig, G. "Further Electron Microscope Observations on Polyethylene III. Smectic Intermediate State During Melting and Crystallization" Colloid Polym Sci. vol. 269 (1991) p. 1118-1125.

Kashiwabara et al., Radiation-Induced Oxidation of Plastics, Radiation Processing of Polymers, Chapter 11, (1992) p. 221-254.

Kato et al. "Structural Changes and Melting Behavior of γ-Irradiated Polyethylene" Japanese Journal of Applied Physics. vol. 20, No. 4. (Apr. 1981) p. 691-697.

Kitamaru et al. "Size and Orientation of Cristallites in Lightly Crosslinked Polyethylene, Crystallized from the Melt Under Uniaxial Compression" Die Makromolekulare Chemie. vol. 175 (1974) p. 255-275.

Kitamaru et al. "Structure and Properties of Lightly Crosslinked Crystalline Polymers Crystallized or Processed Under Molecular Orientation" Journal of Polymer Science: Macromolecular Reviews. vol. 14 (1979) p. 207-264.

Kitamaru et al. "The Properties of Transparent Film Made from Linear Polyethylene by Irradiation Cross-Linking" Properties of Transparent Film. vol. 6, No. 3 (May-Jun. 1973) p. 337-343.

Kitamaru et al. "A Commentary Remark on the Isothermal Crystallization of a Polyethylene Gel from the Stretched Molten State" Bull. Inst. Chem. Res. vol. 46, No. 2 (1968) p. 97-106.

Kurth et al., "Effects of Radiation Sterilization on UHMW-Polyethylene" ANTEC. (1987) p. 1193-1197.

Kurtz et al., Anisotropy and Oxidative Resistance of Highly Crosslinked UHMWPE After Deformation Processing by Solid-State Ram Extrusion, Biomaterials 27 (2006) p. 24-34.

Kurtz et al., Comparison of the Properties of Annealed Crosslinked (Crossfire™) and Conventional Polyethylene as Hip Bearing Materials, Bulletin—Hospital for Joint Diseases, vol. 61, Nos. 1 & 2, (2002-2003) p. 17-26.

Lewis, G. "Properties of Crosslinked Ultra-High-Molecular Weight Polyethylene" Biomaterials. vol. 22 (2001) p. 371-401.

Lin et al. "Review Structure and Plastic Deformation of Polyethylene" Journal of Materials Science. vol. 29 (1994) p. 294-323.

Matsubara et al. "The Wear Properties of High-Density Polyethylene Irradiated by Gamma Rays" Wear. vol. 10 (1967) p. 214-222.

Meyer, B. "Recent Developments in Radiation Sterilizable Plastics" ANTEC. (1987) p. 1190-1192.

Minkova et al. "Blends of Normal High Density and Ultra-High Molecular Weight Polyethylene, γ Irradiated at a Low Dose" Colloid Polym Sci. vol. 268 (1990) p. 1018-1023.

Minkova, L. "DSC of γ-Irradiated Ultra-High Molecular Weight Polyethylene and High Density Polyethylene of Normal Molecular Weight" Colloid Polym Sci. vol. 266 (1988) p. 6-10.

Muratoglu et al. "A Novel Method of Cross-Linking Ultra-High-Molecular Weight Polyethylene to Improve Wear, Reduce Oxidation, and Retain Mechanical Properties" The Journal of Arthroplasty. vol. 16, No. 2 (2001) p. 149-160.

Nakayama et al. "Structure and Mechanical Properties of Ultra-High Molecular Weight Polyethylene Deformed Near Melting Temperature" Pure & Appl. Chem. vol. 63, No. 12 (1991) p. 1793-1804.

Narkis et al., Structure and Tensile Behavior of Irradiation—and Peroxide—Crosslinked Polyethylenes, J. Macromol. Sci.—Phys., vol. B 26, No. 1, (1987) p. 37-58.

Nusbaum et al., The Effects of Radiation Sterilization on the Properties of Ultrahigh Molecular Weight Polyethylene, Journal of Biomedical Materials Research, vol. 13, (1979) p. 557-76.

O'Neill et al. "The Distribution of Oxidation Products in Irradiated Ultra-High Molecular Weight Polyethylene" Polymer Degradation and Stability. vol. 49 (1995) p. 239-244.

Oonishi et al. "Comparison of Wear of UHMWPE Sliding Against Metal and Alumina in Total Hip Prostheses—Wear Test and Clinical Results" 3rd World Biomaterials Congress, Transactions. (Apr. 1988) p. 337.

Oonishi et al. "Comparisons of Wear of UHMW Polyethylene Sliding Against Metal and Alumina in Total Hip Prostheses" Bioceramics. vol. 1 (1989) p. 272-277.

Oonishi et al. "Effect of Cross-Linkage by Gamma Radiation in Heavy Doses to Low Wear Polyethylene in Total Hip Prostheses" Journal of Materials Science: Materials in Medicine. vol. 7 (1996) p. 753-763.

Oonishi et al. "Improvement of Polyethylene by Irradiation in Artificial Joints" Radiat. Phys. Chem. vol. 39, No. 6 (1992) p. 495-504.

Oonishi et al. "In Vivo and In Vitro Wear Behaviour on Weightbearing Surfaces of Polyethylene Sockets Improved by Irradiation in Total Hip Prostheses" Surface Modification Technologies V. (1992) p. 101-112.

Oonishi et al. "SEM Observation on the Clinically Used Gamma-Irradiated Reinforced HDP Socket in Total Hip Replacement" Clinical Implant Materials, Advances in Biomaterials. vol. 9 (1990) p. 379-384.

Oonishi et al. "The Optimum Dose of Gamma Radiation-Heavy Doses to Low Wear Polyethylene in Total Hip Prostheses" Journal of Materials Science Materials in Medicine. vol. 8 (1997) p. 11-18.

Oonishi et al. "Wear Resistance of Gamma-Ray Irradiated U.H.M.W. Polyethylene Socket in Total Hip Prosthesis—Wear Test and Long Term Clinical Results" MRS Int'l. Mtg. on Adv. Mats. vol. 1 (1989) p. 351-356.

Oonishi et al. "Wear Resistance of Gamma-Ray Irradiated UHMWPE Socket in Total Hip Prostheses—Wear Test and Long Term Clinical Results" 3rd World Biomaterials Congress, Transactions. (Apr. 1988) p. 588.

Patel, G. "Acceleration of Radiation-Induced Crosslinking in Polyethylene by Diacetylenes" Radiat. Phys. Chem. vol. 14 (1979) p. 729-735.

Premnath et al. "Gamma Sterilization of UHMWPE Articular Implants: an Analysis of the Oxidation Problem" Biomaterials. vol. 17 (1996) p. 1741-1753.

Prins et al. "Biaxial Orientation of Linear Polyethylenes Using the Compressive Deformation Process" Polymer Engineering & Science. vol. 37, No. 2 (Feb. 1997) p. 261-269.

Rimnac et al. "Chemical and Mechanical Degradation of UHMWPE: Report of the Development of an In Vitro Test" Journal of Applied Biomaterials. vol. 5 (1994) p. 17-21.

Rose et al. "Exploratory Investigations on the Structure Dependence of the Wear Resistance of Polyethylene" Wear. vol. 77 (1982) p. 89-104.

Salovey et al. "Irradiation of Ultra High Molecular Weight Polyethylene" Polymer Preprints. vol. 26, No. 1 (1985) p. 118-119.

Salovey, R. "On the Morphology of Crosslinking Polymers" Polymer Letters. vol. 2 (1964) p. 833-834.

Sandford et al. "Shelf Life Prediction of Radiation Sterilized Medical Devices" ANTEC (1987) p. 1201-1204.

Sawatari et al. "Crosslinking Effect of Ultrahigh Molecular Weight Polyethylene-Low Molecular Weight Polyethylene Blend Films Produced by Gelation/Crystallization From Solutions" Colloid Polym Sci. vol. 269, No. 8 (1991) p. 795-806.

Shen et al. "The Friction and Wear Behavior of Irradiated Very High Molecular Weight Polyethylene" Wear. vol. 30 (1974) p. 349-364.

Shinde et al. "Irradiation of Ultrahigh-Molecular-Weight Polyethylene" Journal of Polymer Science: Polymer Physics Edition. vol. 23 (Feb. 1985) p. 1681-1689.

Silverman, Radiation-Induced and Chemical Crosslinking: A Brief Comparison, Radiation Processing of Polymers, Chap. 2, (1992) p. 15-22.

Streicher, R. "Change in Properties of High Molecular Weight Polyethylenes After Ionizing Irradiation for Sterilization and Modification" Third International Conference on Radiation Processing for Plastics and Rubber (Nov. 1987) (9 pages).

Streicher, R. "Influence of Ionizing Irradiation in Air and Nitrogen for Sterilization of Surgical Grade Polyethylene for Implants" Radiat. Phys. Chem. vol. 31, Nos. 4-6 (1988) p. 693-698.

Streicher, R. "Investigation on Sterilization and Modification of High Molecular Weight Polyethylenes by Ionizing Irradiation" Reprint from beta-gamma Jan. 1989 p. 34-43.

Streicher, R. "Ionizing Irradiation for Sterilization and Modification of High Molecular Weight Polyethylenes" Plastics and Rubber Processing and Applications. vol. 10, (1988) p. 221-229.

Streicher, R. "UHMW—Polyethylen als Werkstoff für artikulierende Komponenten von Gelenkendoprothesen (UHMW Polyethylene Used as a Material for the Articulating Components of Endoprostheses)" Biomed. Technik, vol. 38 (1993) p. 303-313.

Sultan et al., Advances in Crosslinking Technology, Plastics, Rubber and Composites Processing and Applications 21, (1994) p. 65-73.

Sun et al. "Development of an Accelerated Aging Method for Evaluation of Long-term Irradiation Effects on UHMWPE Implants" Howmedica Inc., Pfizer Hospital Products Group. (1996) p. 969-970.

Sun et al. "Development of Stabilized UHMWPE Implants with Improved Oxidation Resistance Via Crosslinking" American Academy of Orthopaedic Surgeons—Scientific Exhibits, Presented at 63rd Annual Meeting of AAOS. (Feb. 22-26, 1996) p. 179-180.

Waldman et al. "Compressive Stress Relaxation Behavior of Irradiated Ultra-High Molecular Weight Polyethylene at 37° C." Journal of Applied Biomaterials. vol. 5 (1994) p. 333-338.

Wang et al. "Melting of Ultrahigh Molecular Weight Polyethylene" Journal of Applied Polymer Science. vol. 34 (1987) p. 593-599.

Ward, I. "New Developments in the Production of High Modulus and High Strength Flexible Polymers" Progr Colloid Polym Sci. vol. 92 (1993) p. 103-110.

Ward, I. "Recent Developments in Oriented Polymers for Biomedical and Engineering Applications" Macromol. Symp. vol. 195 (2003) p. 293-296.

Williams, J. "Radiation Stability of Polypropylene" ANTEC. (1987) p. 1198-1200.

Wilson et al. "Proton Modification of Ultra High Molecular Weight Polyethylene to Promote Crosslinking for Enhanced Chemical and Physical Properties" Mat. Res. Soc. Symp. Proc. vol. 396 (1996) p. 311-316.

Wong et al. "Molecular Deformation Processes in Gel-Spun Polyethylene Fibres" Journal of Materials Science. vol. 29 (1994) p. 520-526.

Yongxiang et al., Crosslinking of Wire and Cable Insulation Using Electron Accelerators, Radiation Processing of Polymers, Chap. 5, (1992) p. 71-92.

Zhao et al. "Effect of Irradiation on Crystallinity and Mechanical Properties of Ultrahigh Molecular Weight Polyethylene" Journal of Applied Polymer Science. vol. 50 (1993) p. 1797-1801.

Zoepfl et al. "Differential Scanning Calorimetry Studies of Irradiated Polyethylene: I. Melting Temperatures and Fusion Endotherms" Journal of Polymer Science: Polymer Chemistry Edition. vol. 22 (1984) p. 2017-2032.

Zoepfl et al. "Differential Scanning Calorimetry Studies of Irradated Polyethylene: II. The Effect of Oxygen" Journal of Polymer Science: Polymer Chemistry Edition. vol. 22 (1984) p. 2033-2045.

Deng, et al. "Effects of Gamma Radiation on Tensile Properties of UHMW Polyethylene" The 20th Annual Meeting of the Society for Biomaterials, Boston, MA, Apr. 1994 (1 page).

Hamilton, et al. "Anisotropic Properties in Ultrahigh Molecular Weight Polyethylene After Cobalt-60 Irradiation" Chapter 6 from Clough, et al. "Irradiation of Polymers" ACS Symposium Series; American Chemical Society, Washington DC, 1996.

Huang, H. "Mechanical Anisotropy of Self-Reinforced Polyethylene Crystallized During Continuous-Melt Extrusion," Journal of Materials Science Letters 18 (1999), pp. 225-228.

Peacock, A. Handbook of Polyethylene: Structures, Properties, and Applications, Chapter 8—Orientation of Polyethylene. Copyright 2000, Marcel Dekker, Inc., New York, NY.

Prins, et al. "Biaxial Orientation of Linear Polyethylenes Using the Compressive Deformation Process," Polymer Engineering and Science, Feb. 1997, vol. 37, No. 2, pp. 261-269.

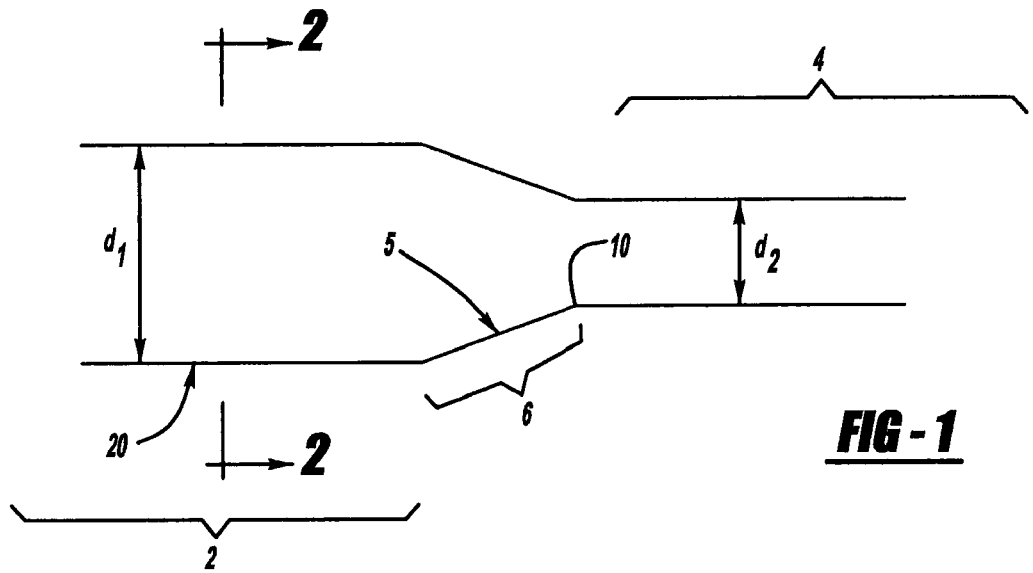
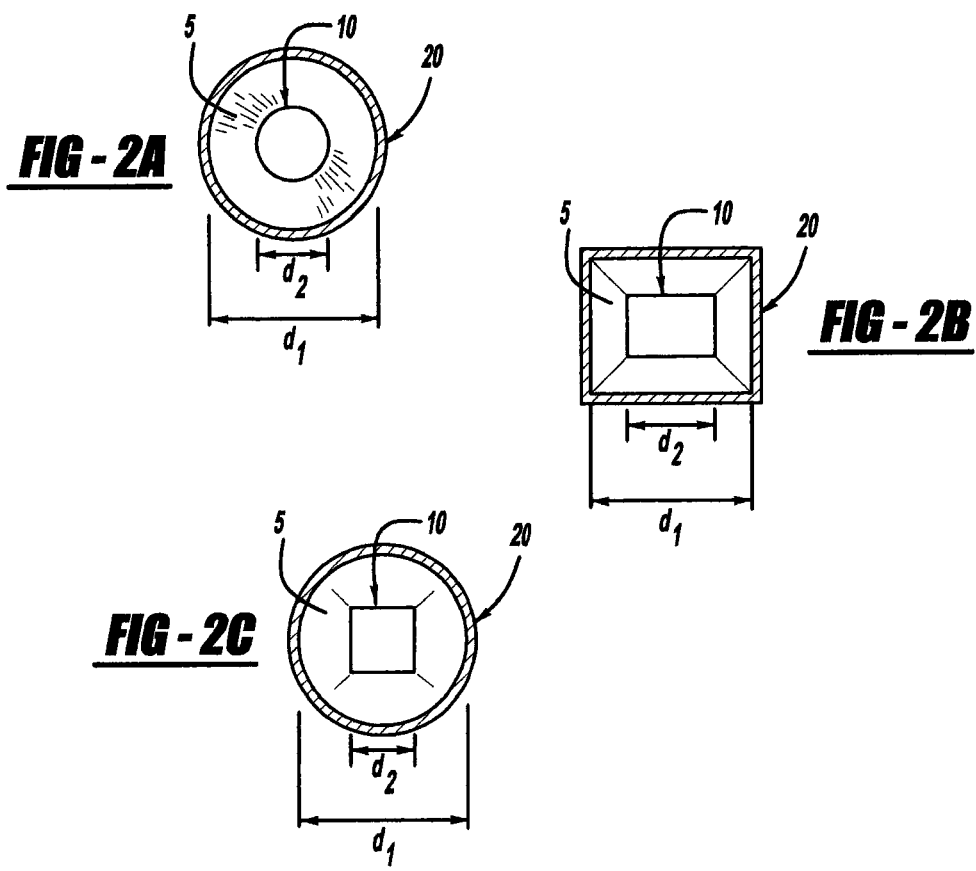

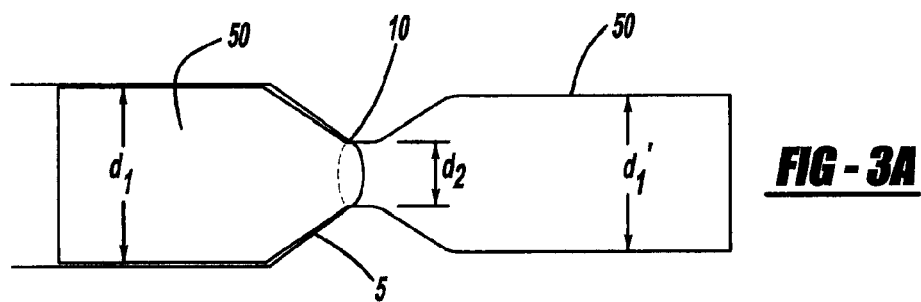
FIG - 3A
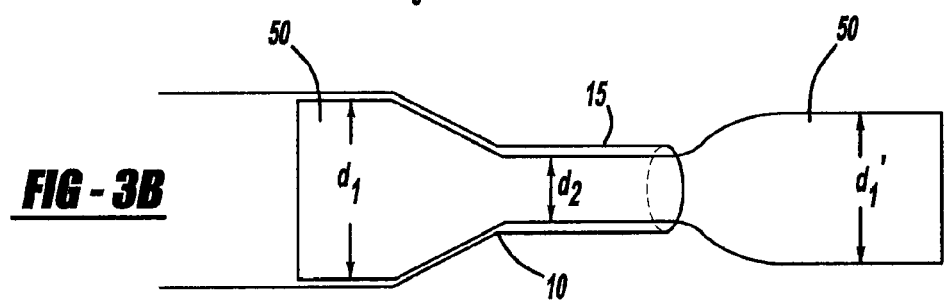
FIG - 3B
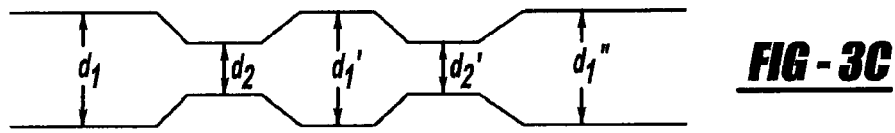
FIG - 3C
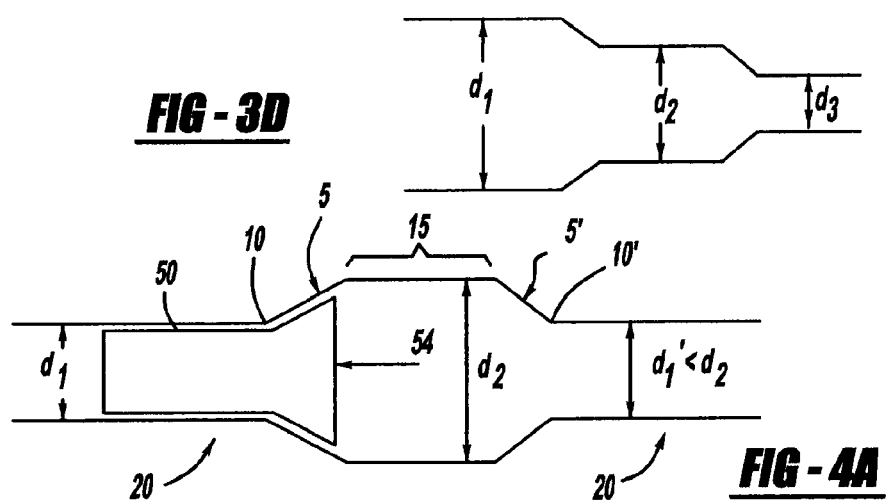
FIG - 3D
FIG - 4A

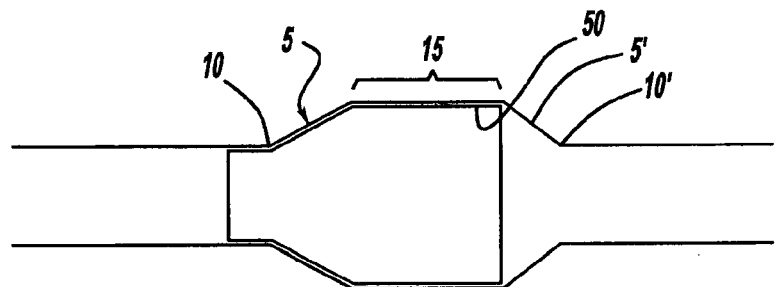
*FIG - 4B*
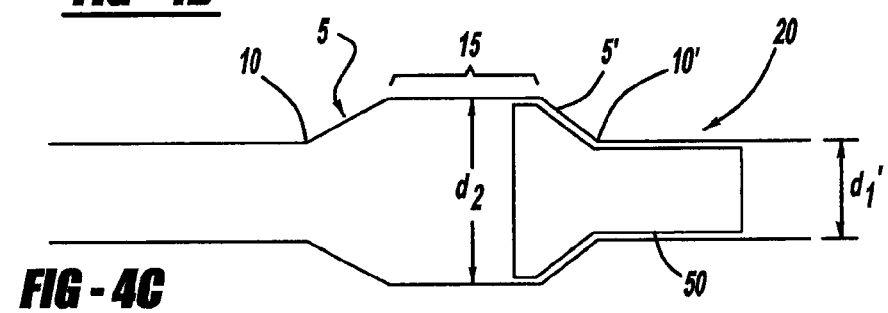
*FIG - 4C*
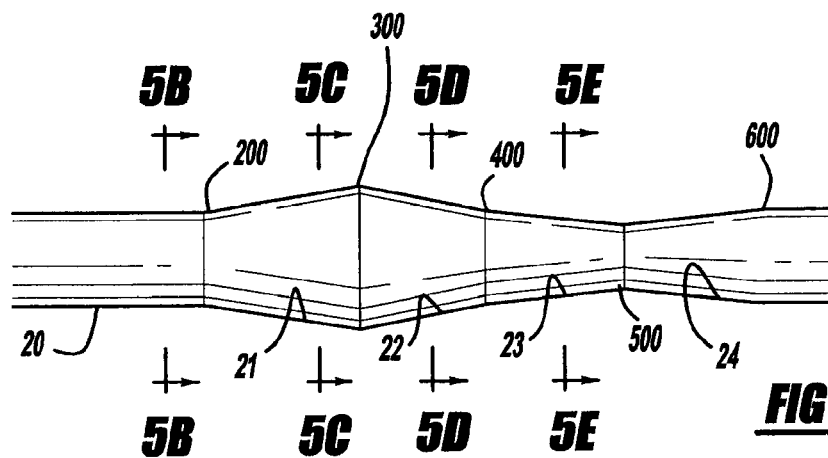
*FIG - 5A*
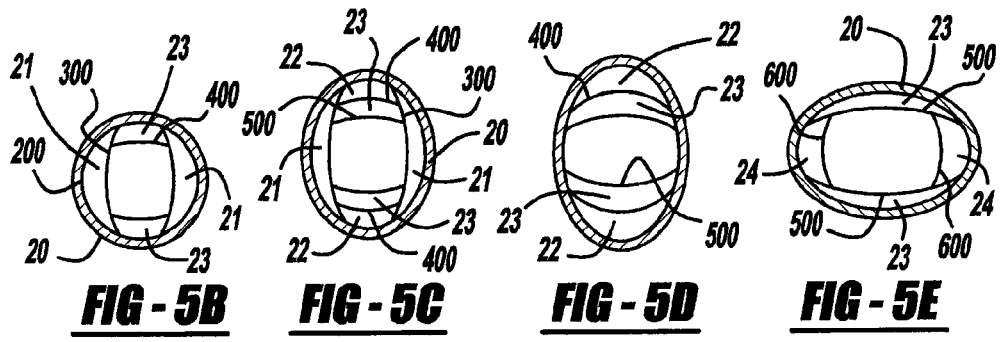
*FIG - 5B*  *FIG - 5C*  *FIG - 5D*  *FIG - 5E*

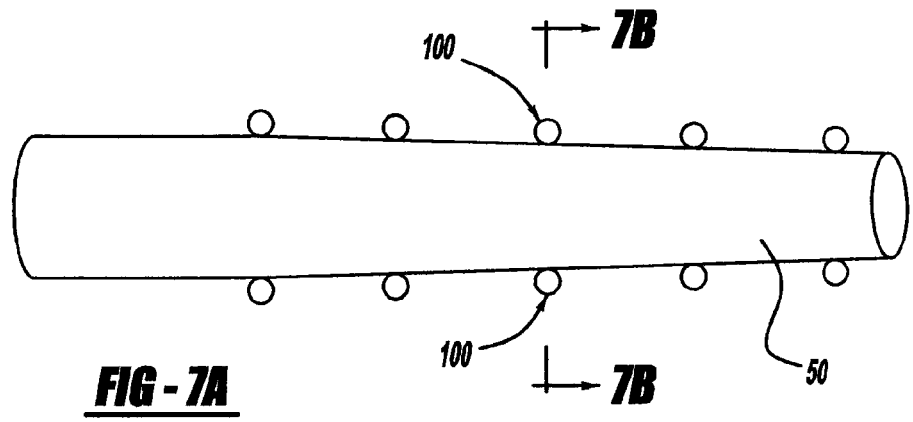
*FIG - 7A*
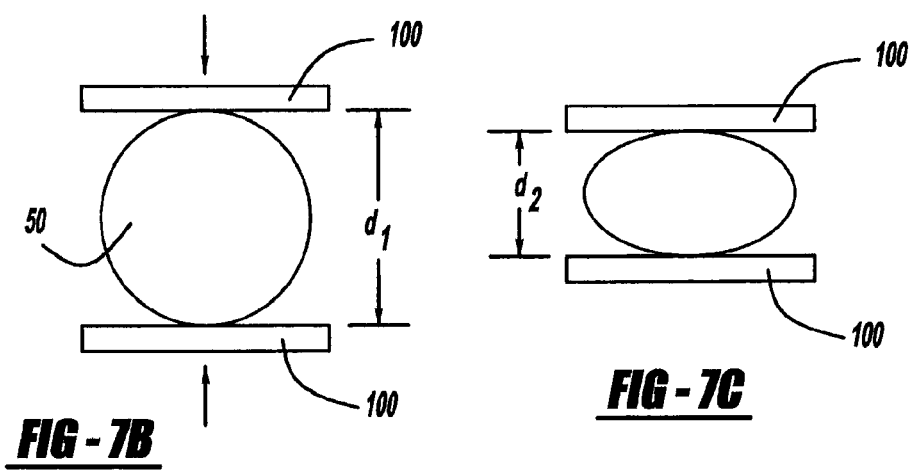
*FIG - 7B*     *FIG - 7C*
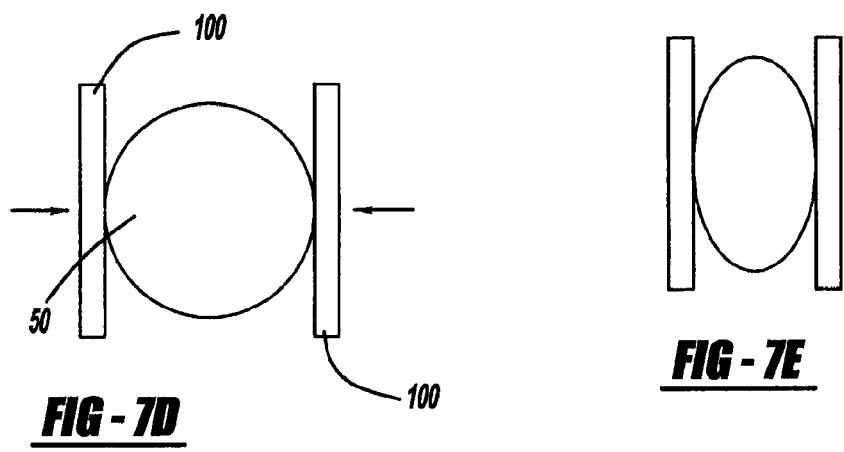
*FIG - 7D*     *FIG - 7E*

SOLID STATE DEFORMATION PROCESSING OF CROSSLINKED HIGH MOLECULAR WEIGHT POLYMERIC MATERIALS

CROSS REFERENCE TO RELATED APPLICATIONS

This application is a divisional of U.S. application Ser. No. 11/402,561 filed Apr. 12, 2006, which is a continuation-in-part of U.S. application Ser. No. 10/963,974 filed Oct. 13, 2004 (now issued U.S. Pat, No. 7,344,672), which claims the benefit of U.S. Provisional Application No. 60/616,811 filed on Oct. 7, 2004. U.S. application Ser. No. 11/402,561 is also a continuation-in-part of U.S. application Ser. No. 10/963,975 filed Oct. 13, 2004 (now issued U.S. Pat. No. 7,462,318), which also claims the benefit of U.S. Provisional Application No. 60/616,811 filed on Oct. 7, 2004. The entire disclosures of each of the above applications are incorporated herein by reference.

INTRODUCTION

The invention relates to crosslinked high molecular weight polymeric material and methods for treating the materials to provide enhanced properties. In particular, the invention provides methods and materials for use in preparing polymeric implants with a high degree of wear and oxidation resistance.

Crosslinked ultra high molecular weight polyethylene (UHMWPE) is now widely used in medical implants such as acetabular components for total hip replacements. There remains interest by the orthopedic community to find alternative methods of processing radiation crosslinked UHMWPE to improve mechanical properties while still retaining wear resistance and oxidative stability in the material.

In U.S. Pat. No. 6,168,626, Hyon et al. report enhancement of the mechanical properties of crosslinked UHMWPE by deformation processing at a compression deformable temperature. After deformation processing, the material is cooled while keeping the deformed state. An oriented UHMWPE molded article is obtained that has an orientation of crystal planes in a direction parallel to the compression plane. The compression is carried out using a suitable die or can be done using a hot press machine.

Polymeric materials such as UHMWPE can be crosslinked to provide materials with superior wear properties, for example. The polymeric materials may be chemically crosslinked or preferably crosslinked with irradiation such as gamma irradiation ($\gamma$-irradiation). The action of $\gamma$-irradiation on the polymer results in the formation of free radicals within the bulk materials. The free radicals provide sites for reactions to crosslink the molecular chains of the bulk materials. It has become recognized that the presence of free radicals, including any free radicals that survive after subsequent heat treatment, are also susceptible to attack by oxygen to form oxidation products. The formation of such oxidation products generally leads to deterioration of mechanical properties.

To completely remove free radicals and provide polymeric materials of high oxidative stability, it is known to heat treat the crosslinked material above the crystalline melting point of the polymer. This has a tendency to destroy or recombine all of the free radicals in the bulk material. As a result, the crosslinked material is highly resistant to oxidative degradation. However, some desirable mechanical properties are lost during the melting step.

It would be desirable to provide materials such as crosslinked UHMWPE that combine a high level of mechanical properties and a high resistance to oxidative degradation.

SUMMARY

A method of solid state deformation processing of crosslinked polymers includes deforming a polymer bulk material by compressing it in a direction orthogonal to a main axis of the bulk material and optionally cooling the bulk material while maintaining the deformation force. When the polymeric material is made of UHMWPE and the crosslinking is by irradiation such as $\gamma$-irradiation, products of the method are particularly suitable for use in bearing components and implants for total hip replacement and the like.

The level of free radicals in the crosslinked polymer is reduced, but normally not eliminated, by working the material with the methods described herein. The bulk material is heated to a compression deformable temperature and is then subjected to a force or pressure that changes a dimension of the bulk material so that the material flows. Although the disclosure is not limited by theory, it is believed the material flow leads to the quenching or reaction of free radicals, leading to a decreased level observed in the solid. Advantageously, the compression deformable temperature can be chosen below the crystalline melt temperature of the polymer so that the heat treatment does not adversely affect physical properties. Despite having a measurable (albeit reduced) level of free radicals, the treated bulk material has a high degree of oxidative stability, in many cases comparable to bulk material that has been melted to remove free radicals.

In one aspect, the invention involves solid state extrusion of an elongate bulk material while the material is at a compression deformable temperature, preferably below the melting point. An extrusion die operates to apply pressure on the bulk material in a direction orthogonal to the main axis, resulting in compression of the material and material flow as discussed. The extruded bulk material is then cooled, optionally while held in the deformed state. Alternatively or in addition, pressure is applied by means of rollers, compression plates, and the like. After cooling, the bulk material is stress relieved by reheating to an annealing temperature to below the melting point, this time without applying pressure.

An oriented UHMWPE molded article can be obtained according to methods of the invention by crosslinking a UHMWPE raw article with a high energy ray such as gamma-irradiation, heating the crosslinked UHMWPE to a compression deformable temperature, and compression deforming the UHMWPE, followed by cooling and solidifying. Preferably, the raw material is in the form of an object, such as a cylinder or bar, characterized by an axial direction parallel to the main axis of the object and by a transverse direction orthogonal to the axial direction. The UHMWPE material and the molded article have a detectable level of free radicals, but are resistant to oxidative degradation evidenced by a very low, preferably undetectable, increase in infrared absorption bands of the UHMWPE material that correspond to formation of carbonyl groups during accelerated aging.

In various embodiments, by compression deforming in a direction orthogonal to the main axis of a bulk material, an anisotropic material is formed wherein mechanical properties in the direction of the main axis differ from mechanical properties in the orthogonal or transverse direction. After stress relieving, mechanical properties can differ by 20% or more in the axial direction as opposed to the orthogonal directions. To illustrate, in various embodiments the tensile strength measured in the axial direction of the bulk material is 20% or more higher than the tensile strength measured in the transverse directions.

Polymers treated by the methods exhibit a desirable combination of high tensile strength and resistance to oxidative degradation. In various embodiments, transverse deformation of UHMWPE, for example, leads to material having a tensile strength at break greater than 50 Mpa and preferably greater than 60 Mpa, measured in the axis orthogonal to the deformation. At the same time, the material is resistant to oxidative degradation, showing in preferred embodiments essentially no change in oxidation index on accelerated aging.

BRIEF DESCRIPTION OF THE DRAWINGS

The present invention will become more fully understood from the detailed description and the accompanying drawings, wherein:

FIG. 1 illustrates the geometry of an extrusion process;

FIG. 2 shows various embodiments of extrusion apparatus and dies; and

FIG. 3 illustrates a extrusion through a decreasing die.

FIG. 4 shows extrusion through an increasing die.

Figure 5F:
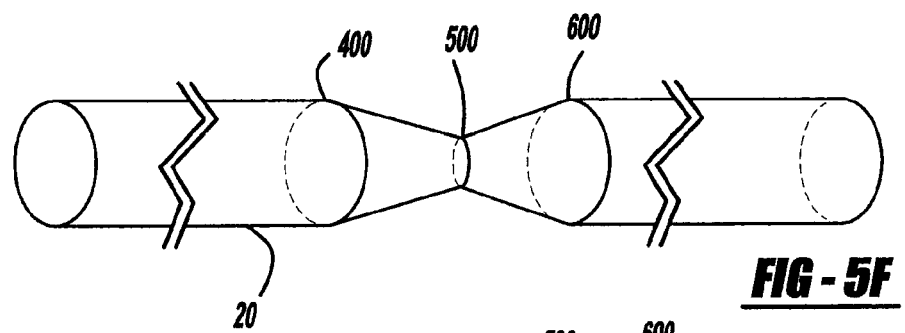
FIG. 5 illustrates extrusion through an isoareal die.

It should be noted that the figures set forth herein are intended to exemplify the general characteristics of materials and methods among those of this invention, for the purpose of the description of such embodiments herein. These figures may not precisely reflect the characteristics of any given embodiment, and are not necessarily intended to define or limit specific embodiments within the scope of this invention.

DESCRIPTION

The headings (such as "Introduction" and "Summary,") used herein are intended only for general organization of topics within the disclosure of the invention, and are not intended to limit the disclosure of the invention or any aspect thereof. In particular, subject matter disclosed in the "Introduction" may include aspects of technology within the scope of the invention, and may not constitute a recitation of prior art. Subject matter disclosed in the "Summary" is not an exhaustive or complete disclosure of the entire scope of the invention or any embodiments thereof. Similarly, subpart headings in the Description are given for convenience of the reader, and are not a representation that information on the topic is to be found exclusively at the heading.

The description and specific examples, while indicating embodiments of the invention, are intended for purposes of illustration only and are not intended to limit the scope of the invention. Moreover, recitation of multiple embodiments having stated features is not intended to exclude other embodiments having additional features, or other embodiments incorporating different combinations of the stated features. Specific Examples are provided for illustrative purposes of how to make, use and practice the compositions and methods of this invention and, unless explicitly stated otherwise, are not intended to be a representation that given embodiments of this invention have, or have not, been made or tested.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, the word "include," and its variants, is intended to be non-limiting, such that recitation of items in a list is not to the exclusion of other like items that may also be useful in the materials, compositions, devices, and methods of this invention.

In one embodiment, a method for reducing the free radical concentration in an irradiated crosslinked bulk polymer is provided. The polymer is in the form of a bulk material that is elongated in an axial direction. Fixing the axial direction defines transverse directions that are orthogonal to the axial direction. The method involves heating the crosslinked bulk material to a compression deformable temperature, followed by applying a force to deform the heated bulk material in a direction orthogonal to the axial direction. Thereafter, the polymer is cooled to a solidification temperature. In various embodiments, the polymer resulting from the processing steps is suitable for further processing into bearing components for medical implants.

In various embodiments, the polymeric material comprises ultrahigh molecular weight polyethylene (UHMWPE). Methods for processing a crosslinked UHMWPE, wherein the UHMWPE is characterized by having a free radical concentration greater than $0.06 \times 10^{15}$ per gram, involve heating the crosslinked UHMWPE to a compression deformable temperature that is preferably below the crystalline melting point of the UHMWPE. The UHMWPE is provided in a bulk form characterized by a dimension $d_1$ in a directional orthogonal to the axial direction. The method involves applying pressure on the UHMWPE in a direction orthogonal to the axial direction to reduce the dimension to a value $d_2$ less than $d_1$. Optionally, the orthogonal pressure is relaxed to permit at least a partial recovery of the dimension $d_2$ to a dimension $d_1'$ greater than $d_2$. Pressure is then optionally reapplied to reduce the dimension to a value $d_2'$ less than $d_1'$. In such an embodiment, $d_2'$ may be less than, equal to, or greater than $d_2$. The steps of releasing and reapplying orthogonal pressure are repeated in some embodiments to provide a desired amount of material flow in the bulk UHMWPE. Thereafter, the crosslinked UHMWPE is cooled to a solidification temperature, and a load bearing medical implant component is machined from the cooled UHMWPE. Characteristically, the component has a load bearing axis substantially coincident with the axial direction of the crosslinked UHMWPE on which the pressure steps are carried out.

In another embodiment, a crosslinked UHMWPE is further characterized by cross-sectional area $A_1$ in a direction orthogonal to the axial direction. In various embodiments, the crosslinked UHMWPE has a concentration of free radicals in the bulk material of greater than $0.06 \times 10^{15}$ spins per gram. The method involves heating the crosslinked UHMWPE to a compression deformable temperature that is preferably below the crystal melting point. Thereafter, pressure is applied on the UHMWPE bulk material in such a way as to increase the dimension to a value $d_2$ greater than $d_1$, and at the same time to increase the cross-sectional are to a value $A_2$ greater than $A_1$. Thereafter the pressure is relieved to permit a return to a value $d_1'$ approximately equal to $d_1$, and in aerial value $A1'$ prime approximately equal to A1. The crosslinked UHMWPE is then cooled to a solidification temperature. Optionally, the pressure applying and pressure relieving steps are repeated as desired to provide an amount of material flow in the bulk material. In various embodiments, the method further involves machining a load bearing component from the treated UHMWPE.

In another embodiment, a crosslinked polymeric material is characterized by a free radical concentration above the detection limit ($0.06 \times 10^{15}$ spins per gram or greater) and the bulk material is characterized as above by an axial direction and further characterized by a cross-sectional area A1 in a transverse section orthogonal to the axial direction. The method involves heating the polymeric material to a compression deformable temperature. The heated material is then deformed by extruding it through a die shaped in such a way so as to change the dimensions of the cross-sectional area of the bulk material, but leave the cross-sectional area essentially unchanged. Thereafter the extruded material is cooled.

In another embodiment, a method of making a medical implant bearing component is provided. The method comprises crosslinking a UHMWPE bulk material to produce a free radical concentration in the UHMWPE greater than $0.06 \times 10^{15}$ spins per gram;

heating the crosslinked UHMWPE to a compression formable temperature;

extruding the heated UHMWPE, in the form of an elongated bulk material comprising a main access defining an axial direction and a cross-section perpendicular to the axial direction though a die that has a shape different from that of the cross-section, but having an area essentially the same as the cross-section, and further processing the UHMWPE to make the bearing component.

In various embodiments described herein, extrusion, compression, and other pressure applying steps are carried out once or multiple times depending on the desired amount of material "working" and flow desired in the bulk material. In various embodiments, it is believed that the material flow caused by the application of pressure as described herein is responsible for quenching of free radicals in the polymeric bulk material. As a result, bulk polymeric materials treated according to the methods described herein tend to have lower free radical concentrations after the deformation pressure is applied.

In various embodiments, deformation pressure is applied to the bulk material in a direction that is perpendicular to the load bearing axis of a medical implant component later to be machined or otherwise produced from the treated bulk material. To illustrate, when the polymeric bulk material is in the form of a rod, cylinder, or bar, deformation is applied according to the methods described herein in a direction that is orthogonal to the main axis of the polymeric bulk material. The main axis of the cylinder, rod, or bar defines the axial direction of the bulk material. In various embodiments, deformation pressure is applied by extrusion, rollers, or compression in a direction perpendicular to the axial direction.

In various embodiments, implants are manufactured using preformed polymeric compositions having the structures described herein and made by the methods described herein. Non-limiting examples of implants include hip joints, knee joints, ankle joints, elbow joints, shoulder joints, spine, temporo-mandibular joints, and finger joints. In hip joints, for example, the preformed polymeric composition can be used to make the acetabular cup or the insert or liner of the cup. In the knee joints, the compositions can be made used to make the tibial plateau, the patellar button, and trunnion or other bearing components depending on the design of the joints. In the ankle joint, the compositions can be used to make the talar surface and other bearing components. In the elbow joint, the compositions can be used to make the radio-numeral or ulno-humeral joint and other bearing components. In the shoulder joint, the compositions can be used to make the glenerohumeral articulation and other bearing components. In the spine, intervertebral disc replacements and facet joint replacements may be made from the compositions.

In various embodiments, the bearing components are made from the polymeric compositions by known methods such as by machining and are incorporated into implants by conventional means.

Polymers

For implants, preferred polymers include those that are wear resistant, have chemical resistance, resist oxidation, and are compatible with physiological structures. In various embodiments, the polymers are polyesters, polymethylmethacrylate, nylons or polyamides, polycarbonates, and polyhydrocarbons such as polyethylene and polypropylene. High molecular weight and ultra high molecular weight polymers are preferred in various embodiments. Non-limiting examples include high molecular weight polyethylene, ultra high molecular weight polyethylene (UHMWPE), and ultra high molecular weight polypropylene. In various embodiments, the polymers have molecular ranges from approximate molecular weight range in the range from about 400,000 to about 10,000,000.

UHMWPE is used in joint replacements because it possesses a low co-efficient of friction, high wear resistance, and compatibility with body tissue. UHMWPE is available commercially, for example from Ticona, Inc. of Bishop Tex., which sells the GUR series of resins. A number of grades are commercially available having molecular weights in the preferred range described above. The resin is made into bulk materials such as bar stock or blocks using various techniques such as compression molding or ram extrusion.

In a non-limiting example, the resin is made into a fully consolidated stock in a series of cold and hot isostatic pressure treatments such as described in England et al., U.S. Pat. No. 5,688,453 and U.S. Pat. No. 5,466,530, the disclosures of which are hereby incorporated by reference. The fully consolidated stock is suitable for subsequent crosslinking and further treatment as described herein.

Crosslinking

According to various embodiments of the invention, a crosslinked polymeric bulk material is further processed in a series of heating, deforming, cooling, and machining steps. The polymeric bulk material can be crosslinked by a variety of chemical and radiation methods.

In various embodiments, chemical crosslinking is accomplished by combining a polymeric material with a crosslinking chemical and subjecting the mixture to temperature sufficient to cause crosslinking to occur. In various embodiments, the chemical crosslinking is accomplished by molding a polymeric material containing the crosslinking chemical. The molding temperature is the temperature at which the polymer is molded. In various embodiments, the molding temperature is at or above the melting temperature of the polymer.

If the crosslinking chemical has a long half-life at the molding temperature, it will decompose slowly, and the resulting free radicals can diffuse in the polymer to form a homogeneous crosslinked network at the molding temperature. Thus, the molding temperature is also preferably high enough to allow the flow of the polymer to occur to distribute or diffuse the crosslinking chemical and the resulting free radicals to form the homogeneous network. For UHMWPE, a preferred molding temperature is between about 130° C. and 220° C. with a molding time of about 1 to 3 hours. In a non-limiting embodiment, the molding temperature and time are 170° C. and 2 hours, respectively.

The crosslinking chemical may be any chemical that decomposes at the molding temperature to form highly reactive intermediates, such as free radicals, that react with the polymers to form a crosslinked network. Examples of free radical generating chemicals include peroxides, peresters, azo compounds, disulfides, dimethacrylates, tetrazenes, and divinylbenzene. Examples of azo compounds are: azobis-isobutyronitrile, azobis-isobutyronitrile, and dimethylazodi-isobutyrate. Examples of peresters are t-butyl peracetate and t-butyl perbenzoate.

Preferably the polymer is crosslinked by treating it with an organic peroxide. Suitable peroxides include 2,5-dimethyl-2,5-bis(tert-butylperoxy)-3-hexyne (Lupersol 130, Atochem Inc., Philadelphia, Pa.); 2,5-dimethyl-2,5-di-(t-butylperoxy)-hexane; t-butyl α-cumyl peroxide; di-butyl peroxide; t-butyl hydroperoxide; benzoyl peroxide; dichlorobenzoyl peroxide; dicumyl peroxide; di-tertiary butyl peroxide; 2,5-dimethyl-2,5-di(peroxy benzoate)hexyne-3; 1,3-bis(t-butyl peroxy isopropyl) benzene; lauroyl peroxide; di-t-amyl peroxide; 1,1-di-(t-butylperoxy) cyclohexane; 2,2-di-(t-butylperoxy) butane; and 2,2-di-(t-amylperoxy)propane. A preferred peroxide is 2,5-dimethyl-2,5-bis(tert-butylperoxy)-3-hexyne. The preferred peroxides have a half-life of between 2 minutes to 1 hour; and more preferably, the half-life is between 5 minutes to 50 minutes at the molding temperature.

Generally, between 0.2 to 5.0 wt % of peroxide is used; more preferably, the range is between 0.5 to 3.0 wt % of peroxide; and most preferably, the range is between 0.6 to 2 wt %.

The peroxide can be dissolved in an inert solvent before being added to the polymer powder. The inert solvent preferably evaporates before the polymer is molded. Examples of such inert solvents are alcohol and acetone.

For convenience, the reaction between the polymer and the crosslinking chemical, such as peroxide, can generally be carried out at molding pressures. Generally, the reactants are incubated at molding temperature, between 1 to 3 hours, and more preferably, for about 2 hours.

The reaction mixture is preferably slowly heated to achieve the molding temperature. After the incubation period, the crosslinked polymer is preferably slowly cooled down to room temperature. For example, the polymer may be left at room temperature and allowed to cool on its own. Slow cooling allows the formation of a stable crystalline structure.

The reaction parameters for crosslinking polymers with peroxide, and the choices of peroxides, can be determined by one skilled in the art. For example, a wide variety of peroxides are available for reaction with polyolefins, and investigations of their relative efficiencies have been reported. Differences in decomposition rates are perhaps the main factor in selecting a particular peroxide for an intended application.

In various embodiments, crosslinking is accomplished by exposing a polymeric bulk material to irradiation. Non-limiting examples of irradiation for crosslinking the polymers include electron beam, x-ray, and γ-irradiation. In various embodiments, γ-irradiation is preferred because the radiation readily penetrates the bulk material. Electron beams can also be used to irradiate the bulk material. With e-beam radiation, the penetration depth depends on the energy of the electron beam, as is well known in the art.

For γ-irradiation, the polymeric bulk material is irradiated in a solid state at a dose of about 0.01 to 100 MRad (0.1 to 1000 kGy), preferably from 0.01 to 10 MRad, using methods known in the art, such as exposure to gamma emissions from an isotope such as $^{60}$Co. In various embodiments, γ-irradiation is carried out at a dose of 0.01 to 6, preferably about 1.5 to 6 MRad. In a non-limiting embodiment, irradiation is to a dose of approximately 5 MRad.

Irradiation of the polymeric bulk material is usually accomplished in an inert atmosphere or vacuum. For example, the polymeric bulk material may be packaged in an oxygen impermeable package during the irradiation step. Inert gases, such as nitrogen, argon, and helium may also be used. When vacuum is used, the packaged material may be subjected to one or more cycles of flushing with an inert gas and applying the vacuum to eliminate oxygen from the package. Examples of package materials include metal foil pouches such as aluminum or Mylar® coating packaging foil, which are available commercially for heat sealed vacuum packaging. Irradiating the polymeric bulk material in an inert atmosphere reduces the effect of oxidation and the accompanying chain scission reactions that can occur during irradiation. Oxidation caused by oxygen present in the atmosphere present in the irradiation is generally limited to the surface of the polymeric material. In general, low levels of surface oxidation can be tolerated, as the oxidized surface can be removed during subsequent machining.

Irradiation such as γ-irradiation can be carried out on polymeric material at specialized installations possessing suitable irradiation equipment. When the irradiation is carried out at a location other than the one in which the further heating, compressing, cooling, and machining operations are to be carried out, the irradiated bulk material is conveniently left in the oxygen impermeable packaging during shipment to the site for further operations.

Bulk Form of the Materials

The crosslinked polymer is provided in a bulk form characterized by an axial direction and a transverse direction orthogonal or perpendicular to the axial direction. In subsequent processing steps, pressure is applied to change a dimension in a transverse direction on the crosslinked bulk material to "work" the material and induce at least some material flow in response to the pressure. In various embodiments, the axial direction corresponds to an elongated dimension or direction of the bulk material, when the material is provided for example in the shape of a cylinder of rod of circular or other cross section. The axial direction is essentially parallel to or coincident with the main axis of the material. In other embodiments, the axial direction does not necessarily correspond visually to an elongated direction, but rather is defined in relation to the direction in which enhanced physical properties such as tensile strength are developed. In preferred embodiments, for example, load bearing components are produced from the treated bulk material in an orientation where the load bearing axis corresponds approximately or exactly to the axial direction.

For convenience of reference, a set of 3-D orthogonal axes is set up with one of the axes coincident with the axial direction. To illustrate, the "z" axis can be taken as coincident with the main cylindrical axis of bulk material in the form of a cylinder. The other two axes lie in a plane perpendicular to the axial direction. Thus the "x" and "y" axes lie perpendicular to the axial direction, and represent transverse axes or transverse directions in the bulk material. The orientation of "x and "y" axes is arbitrary in the transverse plane. When the cross section of the bulk material is circular, all possible orientations of the "x" and "y" transverse axes are equivalent. With other shapes, "x" and "y" components of the bulk material depend on the arbitrarily chosen axes. But in all cases, the shape of the transverse cross section of the bulk material, and the changes in dimension upon application of pressure along those axes, can be expressed as a combination on the basis of the "x" and "y" axes. In various embodiments, a change in dimension in response to an applied pressure occurs in the direction of the applied pressure, which direction can be expressed algebraically and vectorally as a combination of "x" and "y" components.

In various embodiments, the axial direction is constant throughout the bulk material. This is the case for, say, straight cylinders where the (straight) main axis of the cylinder is taken as the axial direction. This is a preferred arrangement. But the bulk material can also be provided in the form of an elongated body where the main axis changes direction along the axial direction. Such would be the case for bent or curved rods, for tori, and for other closed shapes, by way of non-limiting example. For such bulk materials, the transverse directions are still defined as those directions which are at right angles to the axial direction, whatever the local orientation of the axial direction of the bulk material. The methods described herein are readily adapted to provide changes in dimensions in the bulk material at right angles to the (local) axial direction.

The shape of the cross section transverse to the axial direction of the bulk material is not particular limited and includes circles and their topological equivalents (such as ovals, ovoids, ellipses, and other areas bounded by a closed curve), as well as other shapes. Non-limiting examples of shapes include regular and non-regular polygons (e.g. squares, rectangles, rhombus, and trapezoids for four sided figures), stars, convex shapes, and concave shapes. Certain shapes are preferred because of their relative ease of manufacture. Such include circular cross-sections, readily produced by RAM extrusion for example.

The axial direction is the direction in which higher tensile strength is developed, as described further below. In this aspect, the axial direction of the bulk material is the direction perpendicular to the dimensional change in the transverse direction that results from application of pressure. In various embodiments, application of pressure or force orthogonal to the axial direction creates an anisotropic material, characterized by higher tensile strength in the axial than in the transverse direction.

The axial direction of the bulk material also defines the preferred direction in which implant bearing components such as acetabular cups are to be machined. That is, bearing components are preferably made or machined from the treated bulk polymer in an orientation where the higher tensile strength axis of the polymeric bulk material corresponds to the load bearing axis or direction of the bearing component of the implant in vivo.

In an exemplary embodiment, the bulk material is in the form of a rod or cylinder having a circular cross section. The axial direction is parallel to the main axis of the cylinder, while the transverse directions are at right angles to the axial direction. In other words, the existence of the axial direction defines an orthogonal direction referred to as "transverse" in this application. When the cross section of the bulk material is isotropic as in the case of a cylinder, the transverse direction can be described as "radial", and the transverse axis as a radial axis. The main axis of the bulk material can also be called the longitudinal axis. As used here, the longitudinal axis is parallel to the axial direction.

In the non-limiting case of a rod or cylinder, a cross section of the bulk material perpendicular to the axial direction or longitudinal axis is a circle. Other bulk materials characterized by an axial direction may be used that have other perpendicular cross sections. In a non-limiting example, a square cylinder can be provided that has a square cross section perpendicular to the axial direction. Other bulk materials characterized by an axial direction can have rectangular, polygonal, star, lobed, and other cross sections perpendicular to the axial direction.

In various embodiments, the axial direction of the bulk polymeric material is elongated compared to the orthogonal or radial direction. For example, in the case of UHMWPE, a commercially available bulk material is a cylinder approximately 3 inches in diameter and 14 inches in length. The length corresponds to the axial direction and the diameter corresponds to the radial direction. As described below, bearing components for implants are preferably machined from billets cut in the axial direction. For efficiency in manufacturing it is convenient to produce a number of bearing components from a single bulk material treated by the methods of the invention. For this reason, the bulk material is usually to be extended in an axial direction so as to be able to cut a plurality of billets from the material for use in further machining of the bearing components.

As described above, bulk material characterized by an axial direction is further characterized as having a variety of cross sectional areas perpendicular to the axial direction. In various embodiments, the dimensions of the cross sectional areas perpendicular to the axial direction are more or less constant along the axial direction from the beginning to the end or from the top to the bottom of the bulk material. In various other embodiments, bulk materials may be provided to have cross sectional areas that vary along the length or axial direction of the bulk material. In the case where the cross sectional area of the bulk material is constant along the axial direction of the bulk material, compressive force applied as described below will generally be applied to the bulk material in a direction perpendicular to the axial direction. In the case where the cross sectional area varies along the axial direction of the bulk material, compressive force applied to the bulk material may have a component in the axial direction due to the geometry of the bulk material. However, in all cases at least a component of the compressive force will be applied on the bulk material in a direction orthogonal to the axial direction.

Pre-Heating

Before further processing, the crosslinked polymer is heated to a compression deformable temperature. The compression deformable temperature is temperature at which the polymeric bulk material softens and can flow under the application of a compressive source to change dimension in the direction the compressive force is applied. For UHMWPE and other polymeric materials, the compression deformable temperature is concretely from about the melting point minus 50° C. to the melting point plus 80° C.

In various embodiments, the compression deformable temperature is below the melting point of the polymeric material. Examples of the compression deformable temperature include from the melting point to 10° C. below the melting point, from the melting point to 20° C. below the melting point, from the melting point to 30° C. below the melting point, and from the melting point to 40° C. below the melting point. For UHMWPE, the compression deformable temperature is preferably above 80° C., or from about 86° C. to about 136° C., since the melting temperature of the UHMWPE is about 136° C. to 139° C. In various embodiments, the compression deformable temperature of UHMWPE lies from about 90° C. to 135° C., preferably about 100° C. to 130° C. A preferred temperature is 125-135° C., or 130° C.±5° C.

In various embodiments, the crosslinked material is heated to a compression deformable temperature above the melting point of the polymer. For UHMWPE and other polymeric materials, such a compression deformable temperature is from just above the melting point to a temperature about 80°

C. higher than the melting point. For example, UHMWPE can be heated to a temperature of 160° C. to 220° C. or 180° C. to 200° C.

In various embodiments, it is preferred to heat the bulk polymeric material to a compression deformation temperature close to but not higher than the melting point. In various embodiments, the compression deformable temperature is between the melting point and a temperature 20° C. lower than the melting point, or between the melting point and a temperature 10° C. lower than the melting point.

The crosslinked bulk material can be heated to a compression deformable temperature in a deformation chamber as illustrated in the figures, or it can be preheated in an oven to the compression deformable temperature. In various embodiments, the bulk material is heated to a temperature just below the melting point, such as the melting point minus 5° or the melting point minus 10° and placed in a heated deformation chamber. The deformation chamber preferably maintains a compression deformable temperature. If desired, the deformation chamber can be heated or thermostatted to maintain a constant temperature. Alternatively, the deformation chamber is not itself heated but has sufficient insulating properties to maintain the bulk material at a compression deformable temperature during the course of pressure application described below. In various embodiments, the temperature of the deformation chamber is held at several degrees below the melting temperature to avoid melting.

Deformation

When the crosslinked bulk material is at a compression deformable temperature, pressure is applied to the bulk material to induce a dimensional change in a direction orthogonal to the axial direction. The dimensions of the bulk material change in response to the application of pressure, which results in "working" of the crosslinked material with material flow of the heated bulk material. Force (or, equivalently, pressure, which is force divided by area) is applied so that least one component of the dimension change is orthogonal to the axial direction of the bulk material, with the dimensional change being either positive or negative. To illustrate, for cylindrical rods and other bulk materials that have a constant cross section along the axial direction of the bulk material, compression force is applied in a direction perpendicular to the axial direction in order to decrease an axial dimension Any suitable methods may be used to apply the compression force in a direction orthogonal to the axial direction. Non-limiting examples include extrusion through dies and the use of rollers, compression plates, clamps, and equivalent means.

Extrusion

In various embodiments, deforming force is applied in the direction orthogonal to the axial direction of the bulk material by extruding the bulk material through a die or series of dies. Extrusion through the die or dies is carried out in the axial direction of the bulk material. Suitable dies can be manufactured by traditional machining methods, by electrical discharge machining, or by other techniques well known in the machine tool art.

A die used in the extrusion processes has a shape and size selected to apply pressure in a transverse direction to the bulk material in the desired fashion. Examples of shapes include, without limitation, circles and their topological equivalents, shapes bounded by closed curves, shapes bounded by a closed curve made up of straight segments and curved segments, regular polygons, and non-regular polygons. Without limitation, the die has one or more of concave shapes, convex shapes, smooth shapes (for example, having a continuous derivative), smooth shape with a kink or kinks (for example, points where the derivative is non-continuous), or shapes bounded by straight lines (e.g. regular and non-regular polygons). In various embodiments, certain die shapes are preferred for their ease of manufacture. The choice of die shape is also to be made in consideration of compatibility with the shape and size of the bulk material to be worked.

The act of extruding converts the pressure of an extrusion ram in an axial direction to pressure in the transverse direction applied by the die. Depending on the configuration of the die used, and the cross-sectional shape and area of the workpiece in relation to the cross-sectional shape and area of the die, extrusion is accomplished with a reduction in cross-sectional area (a "reducing die"), with an increase in cross-sectional area (an "increasing die") or with no change in cross-sectional area (an "isoareal die"). Various extrusion embodiments are illustrated in the Figures. It is to be noted that the Figures are not necessarily drawn to scale and do not necessarily represent preferred configurations for any individual embodiment; the Figures are used to illustrate the concepts.

Reducing Die

A reducing die has a cross-sectional area that is less than the cross-sectional area of the piece to be extruded through the die. During extrusion through a reducing die, pressure exerted on the bulk material in a direction orthogonal to the axial direction causes at least one transverse dimension of the bulk material to be reduced compared to the original dimension of the bulk material. In other words, the diameter or other transverse dimension of the bulk material after extrusion is less than the dimension before extrusion.

The relative reduction in the dimension of the bulk material in the transverse directions can be expressed as a ratio of the original dimension $d_1$ to the reduced dimension $d_2$. Depending on the method of reducing the dimension by applying compressive force, the numeric value of the ratio $d_1/d_2$ can be referred to as a draw ratio or a diametral compression. For extrusion, it is common practice to refer to a draw ratio; unless stated otherwise from context, the term draw ratio will be used here to refer to all geometries.

It is to be understood that the transverse direction (the direction orthogonal to the axial direction) itself contains two axes that can be drawn at right angles to the longitudinal axis. In various embodiments, the bulk material can be deformed by a different amount along the two transverse axes, and a draw ratio can be defined for both axes (or, equivalently, any linear combination of the two axes). The orientation of the transverse axes is arbitrary; if needed for analysis, the axes can be selected to simplify the geometry of the applied forces. When the cross section of the bulk material is circular, equal deformation force can be applied in all transverse directions by extruding through a circular reducing die. In this non-limiting case, the dimension $d_2$ corresponds to the radius or diameter of the extruded material, and the draw ratio is the fraction defined by dividing $d_1$ by $d_2$.

In various embodiments, the draw ratio is 1.1 or higher, and less than about 3. In various embodiments, the draw ratio is 1.2 or higher, and is preferably about 1.2 to 1.8. It is about 1.5 in a non-limiting example. Minimum levels of draw ratio provide sufficient material flow in the crosslinked material to provide benefits described herein. As the crosslinked material is "worked" to a greater extent, the dimensions in the transverse direction change to a greater extent, thus increasing the calculated draw ratio. As the draw ratio is increased, a point is eventually reached at which the strain introduced by the dimension change is too great and the properties of the crosslinked polymeric materials deteriorate. Accordingly, in various embodiments the draw ratio is 3.0 or less, 2.5 or less, and preferably about 2.0 or less. In a preferred embodiment, the compressive force is applied more or less isotropically around the bulk material in a direction transverse to a longitudinal axis. Accordingly, the reduction in dimension will usually apply in all transverse directions. To illustrate, a circular cross section remains round but is reduced in diameter, while a polygonal cross section such as a square or rectangle is reduced on all sides.

When compressive force is applied anisotropically with a reducing die, the two dimensions of the workpiece orthogonal to the long axial direction change by different amounts. At least one is reduced to such an extent that the cross-sectional area of the die is less than that of the workpiece. Examples of dies that apply force or pressure anisotropically include ovals, rectangles, and other "asymmetric" shapes. Asymmetric shapes include those resulting from deformation of a circle, such as ellipses, ovals, and the like.

The geometry of extrusion through a reducing die is illustrated in schematic form in FIGS. 1 and 2. A reducing die 6 is disposed between a deformation chamber 2 and a holding chamber 4. As shown, the holding chamber has the same diameter as the die. In various embodiments it is equipped with water or other cooling means to slowly cool the extruded material from its compression deformable temperature. The figure is shown in a cross sectional view to illustrate that the reducing die 6 reduces the diameter or dimension of the extruded material from an original dimension $d_1$ to an extruded dimension $d_2$, as extrusion is from left to right in the Figure. As the crosslinked heated bulk material passes from the deformation chamber through the reducing die 6, the material flows by the die wall 5 that leads to a constriction 10 having the diameter $d_2$ of the cooling chamber 4.

Various geometries of the reducing die are illustrated in non-limiting form in FIG. 2. FIGS. 2a to 2e show the relative configuration of the deformation chamber wall 20 and the die constriction 10. The die wall 5 is seen to connect the cooling deformation chamber to the cooling chamber. In FIG. 2a, the cross section of both the deformation chamber 2 and cooling chamber 4 are circular (indicated with the illustration of the relative disposition of the chamber wall 20 and the restriction 10), with dimensions $d_1$ and $d_2$ corresponding to their respective diameters. In FIG. 2b, the deformation chamber is square or rectangular characterized by a dimension $d_1$ that can be arbitrarily taken along a diagonal or along a side. In FIG. 2b, the restriction 10 is also rectangular but having lower dimension $d_2$. FIGS. 2c through 2e illustrate other combinations of circular, square, and triangular deformations and cooling chambers connected by reducing dies 6 having a die wall 5, and are offered by way of non-limiting example.

As noted above, the bulk material in the deformation chamber 2 is held at a compression deformable temperature. At such a temperature, the material can flow in response to pressure exerted on the material. When the compression deformable temperature is below the melting point, the material undergoes a solid state flow through the reducing die 6. Pressure or force applied to the end of the bar by the ram is translated by the die into compressive force that reduces the dimension of the bulk material in the transverse direction. For convenience, the deformation chamber illustrated in FIG. 1 can be sized to match relatively closely the diameter or dimension $d_1$ of the bulk material to be extruded.

When the material is extruded into a holding chamber as illustrated in FIG. 1, as noted the material can be cooled down while being held in a deformed state to the extent that $d_2$ is less than $d_1$. Alternatively, the material can extruded through the die into a region of ambient pressure, allowing the bulk material to immediately recover from the dimension change from $d_1$ to $d_2$. When not held at a reduced dimension, the extruded crosslinked material tends to return at least somewhat to its original shape, so that $d_2$ tends to recover approximately to its original dimension $d_1$. Normally, the recovery occurs within seconds of being extruded through the die into ambient pressure conditions.

Extruding the bulk material at draw ratios of about 1.1 or higher as described above works the extruded material by inducing material flow as the dimensions are reduced by passing through the extrusion die. In various embodiments, the amount of the working is determined by the relative draw ratio. Thus, preferred draw ratios are 1.1 or higher and less than about 3. In some embodiments, it is desired to increase the working of the material without causing too high a strain on the part, for example by extruding at a high draw ratio.

One way of increasing the working of the material without overly increasing the draw ratio is to carry out a sequential extrusion of the bulk material through a die. In a simple embodiment, the method involves extruding the bulk material through the reducing die, collecting the material as it comes out the die, and providing the material as input to another die or the same die. In this way, the material can be re-extruded to provide a desired amount of working, which leads to reduction in the level of free radicals in the material. Non-limiting embodiments of the sequential extrusion are illustrated in FIG. 3.

FIG. 3a shows extrusion of a bulk material 50 through a constriction 10 in a die that reduces the dimension from $d_1$ to $d_2$ in the transverse direction. Upon passing out of the die, the pressure applied by the constriction is relieved (by passing into a region of ambient pressure) and the dimension of the bulk material tends to increase to a dimension $d_1'$, which is generally the same as or slightly less than the original dimension $d_1$. If it is desired to work the bulk material further, the bulk material 50 can be re-extruded through the die shown in FIG. 3a. In the second extrusion, a bulk material of dimension $d_1'$ is extruded through the reducing die. After emerging from the extruding die, the diameter is given as $d_1''$, which as before tends to be about the same or slightly less than $d_1'$. In this way, an arbitrary number of extrusions can be carried out on a bulk material 50 to provide a desired (reduced) level of free radicals in the bulk material, the lower level arising from the working of the material by extruding through the die.

An alternative embodiment is shown in FIG. 3b. Here, the bulk material 50 is extruded through a constriction 10 into a chamber 15 having a dimension $d_2$ of less than the original dimension $d_1$. However, in FIG. 3b, the extrusion apparatus is sized so that the bulk material has a higher volume than chamber 15. As a result, during extrusion the bulk material is extruded out of the apparatus, whereby it regains dimension to a value $d_1'$ that, as before, is approximately the same as or slightly less than the original $d_1$. The worked materials 50 can be re-extruded as before.

The examples shown in 3a and 3b are characterized as multiple extrusions through a single die. Working can also be provided by extruding through a series of dies as illustrated in non-limiting fashion in FIGS. 3c and 3d. FIG. 3c shows a series of dies that take the diameter of the bulk material from an original diameter $d_1$ to a first constricted diameter $d_2$ to a second expanded $d_1'$ to a second restricted diameter $d_2'$ and finally to a final dimension $d_1''$. In various embodiments, it is contemplated to extrude the bulk material (not shown) from the series of dies to ambient conditions where the diameter returns approximately to the original diameter $d_1$. Another embodiment is shown in non-limiting fashion in FIG. 3d, where a series of dies is set up to take bulk material from an original dimension $d_1$ to a second dimension $d_2$ to a third dimension $d_3$. As before, it is contemplated to extrude the bulk material through the apparatus, whereby the dimension recovers to a value close to or slightly less than the original dimension $d_1$. If desired, material that has been passed through a series of dies as shown in non-limiting fashion in FIGS. 3c and 3d can be re-extruded through the same apparatus or through apparatus such as shown in FIGS. 3a and 3b. In all cases, re-extrusion works the material further, which generally leads to a reduction in concentration of free radicals, for example in the crystalline regions of the bulk material.

As with the single dies illustrated in FIGS. 1 and 2, in various embodiments the material is extruded through a series of dies as illustrated in FIG. 3, but into a holding chamber or other device to maintain the dimension of the extruded material at a reduced value compared to the original dimension $d_1$. The material is then cooled while maintaining the compressed state.

Increasing Die

Another way of working the crosslinked material to reduce the level of free radicals is to induce flow in the bulk material by extruding it in an increasing die. When the temperature is below the crystalline melting point of the UHMWPE or other crosslinked material, the flow in the bulk material is characterized as solid state flow. The method is illustrated in non-limiting fashion in FIG. 4. In FIG. 4a, shown in cross section, the bulk material 50 is extruded through a restriction 10 into an area of increasing volume defined by the walls 5 to a chamber 15 that is characterized by a dimension $d_2$ that is greater than dimension $d_1$. As illustrated, it is normally desirable to provide at least a slight amount of back pressure 54 to cause the bulk material to flow outward to fill the chamber 15. Back pressure is provided by any suitable means, such as without limitation with a ram, with a sacrificial puck set up as described below, or with fluid pressure. Upon removal of the pressure 54, for example by extruding it out of the extrusion apparatus, the dimension $d_2$ tends to return to a value close to the original dimension $d_1$. As drawn in FIG. 4, the extrusion apparatus further comprises a decreasing wall 5' leading to a second constriction 10' that defines a reducing die as illustrated for example in FIG. 3. In a preferred embodiment, after extruding through an increasing die as shown in FIG. 4a and into the chamber 15 (FIG. 4b), the bulk material is further extruded through a decreasing die as further illustrated in FIG. 4c to bring the dimension back to a value $d_1'$ which is less than $d_2$. Alternatively or in addition, the bulk material is extruded through a series of increasing dies analogous to that shown in FIG. 3d for the decreasing die. In various embodiments, the bulk material 50 is worked by extruding through a sequence of increasing and decreasing dies as illustrated schematically in FIG. 4.

Isoareal Die

In a particular embodiment, the bulk material is worked by extruding through a die that changes the dimensions of the cross section of the elongated bulk material being extruded, but does not substantially change the cross sectional area. Working of the bulk material is provided by extruding, although no net change in area occurs. In various embodiments, the isoareal extrusion is advantageous because the extrusion requires less ramming force, since there is less resistance to flow because of the small or zero value net area change in the cross section.

Thinking in terms of the x and y axis of the cross sectional area, it is clear that for an isoareal extrusion through a restriction, it is necessary that at least one dimension of the cross section decrease while another increase. The die itself can be conceptualized as providing a first cross sectional area, which in most practical applications is substantially the same as the cross section of the bulk material to be worked. The isoareal die also provides a second cross sectional area which has the same cross sectional area, but has different dimensions. In a simple illustration the first shape is a circle and the second shape is an oval or ellipse having the same area as the circle. The dimension of the circle is conveniently given by a radius or diameter, while the dimensions of the oval are provided by a major and minor axis. The values of diameter, and a major and minor axes are selected to give isoareal circles and ovals according to well known geometrical principles. Of course, the method can be generalized to provide isoareal shapes for any arbitrary starting configuration of the bulk material. As noted, a common bulk form of crosslinked UHMWPE is a cylinder of approximately 3 inches in diameter and 14 inches in length. Accordingly, isoareal extrusion is provided for the exemplary crosslinked bulk material if the second shape has a cross sectional area of approximately 7.06 square inches ($\pi d^2/4$ when the diameter d is 3 inches).

As a physical practicality, there is a transition zone between the first die shape and the second die shape. In preferred embodiments, the cross sectional area in this transition zone is the same as the first shape and the second shape, as it "morphs" from the first shape to the second shape to provide isoareal restriction. In various embodiments, the absolute requirement of mathematical precision in the machining of such die shapes and transitions zones is relaxed slightly; the key feature of this aspect is that, due to the approximately equal areas of the two shapes, extrusion through the die takes place with a minimum of power input to provide advantages as described herein.

The geometry and set up of isoareal dies is illustrated in non-limiting fashion in FIG. 5. FIG. 5a shows an extrusion apparatus, where 20 is the wall of an elliptical die tool. The extrusion apparatus is illustrated showing isoareal extrusion shapes indicated as 200, 300, 400, 500, and 600. The shapes are connected by transition zones having inner walls 21, 22, 23, and 24. A view along cut line 5b illustrates that in relation to circular shape 200, shape 300 is a vertical oval. The view along 5c shows that shape 400 goes back to a circle. The view along line 5d shows that isoareal shape 500 is an oval turned at 90° to the oval of shape 300. The view along line 5e shows shape 600 is again a circle. Working of a crosslinked bulk material is accomplished as before by pushing a bulk material (not shown) through a die or series of dies illustrated as 200, 300, 400, 500, and 600 in FIG. 5. As before, the bulk material can be further worked by subsequent re-extrusion through the same apparatus. As illustrated with isoareal extrusion, in various embodiments it is preferred to provide a plurality of isoareal restriction steps, including changes in shape along different axes. This provides material flow in more than one dimension and tends to lead to better free radical concentration reduction induced by the material flow.

Figure 5G:
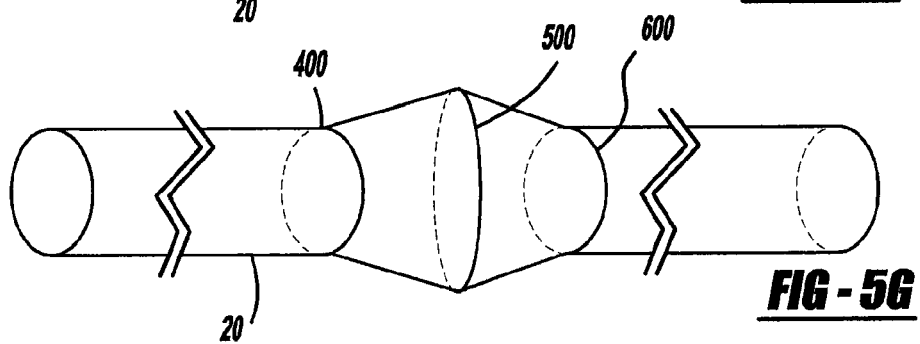
Figure 6A:
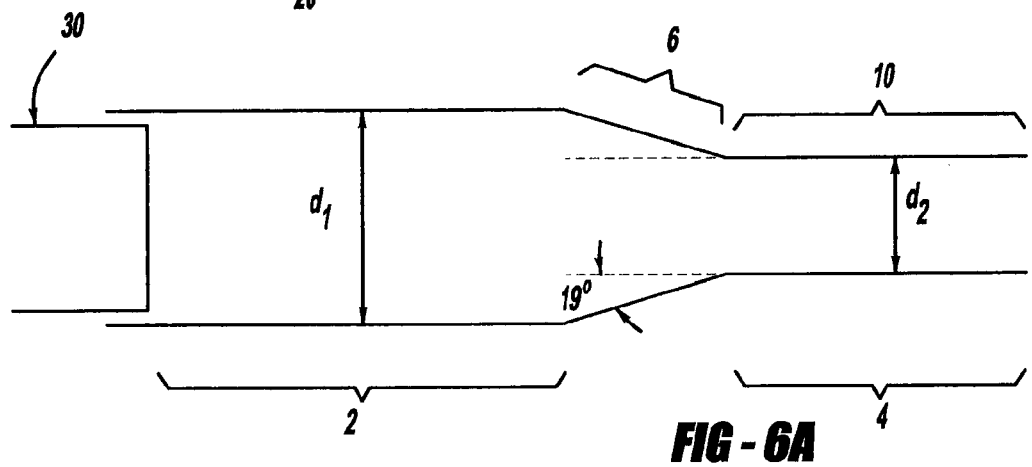
FIG. 6 illustrates use of sacrificial puck in certain embodiments.
Figure 6B:
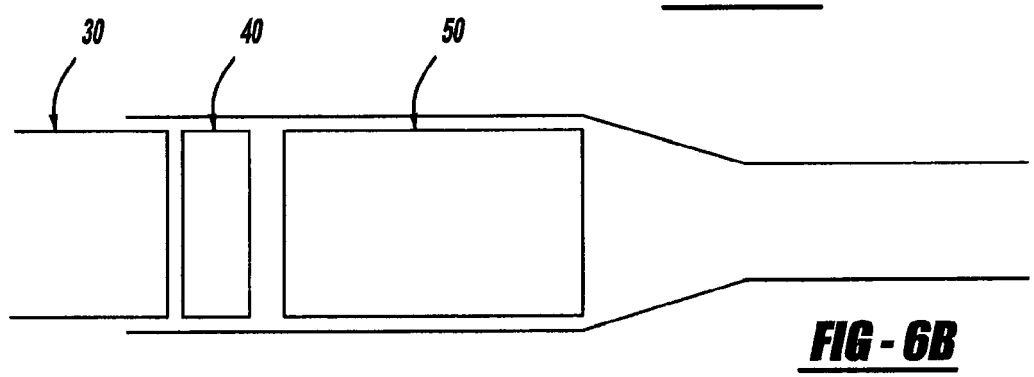
Figure 6C:
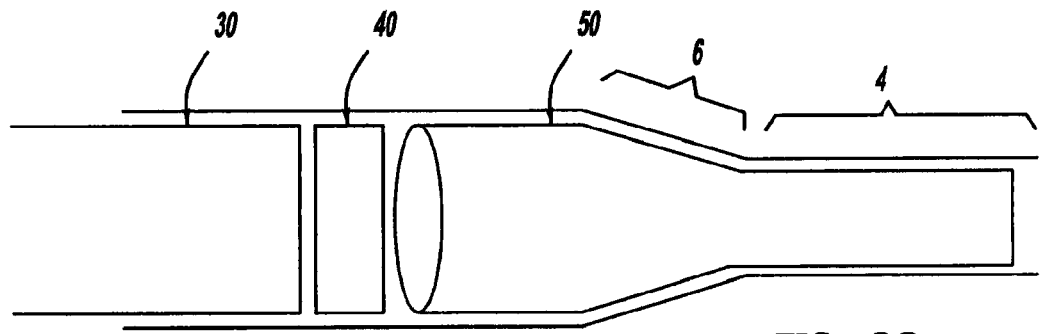
Figure 6D:
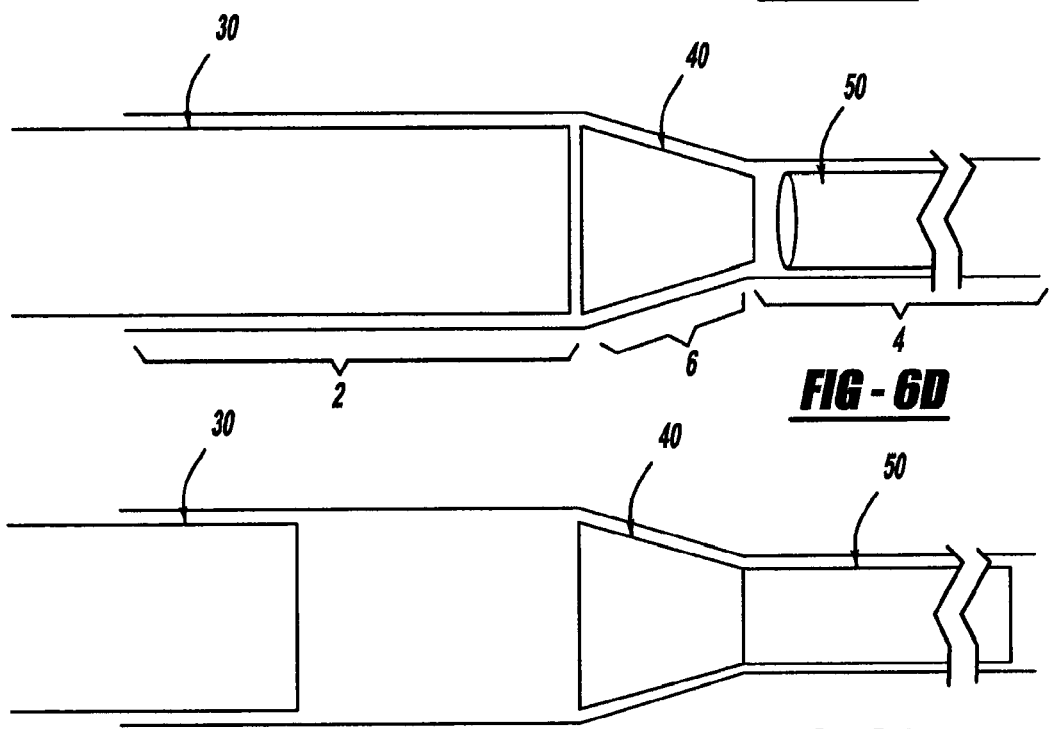
Figure 6E:
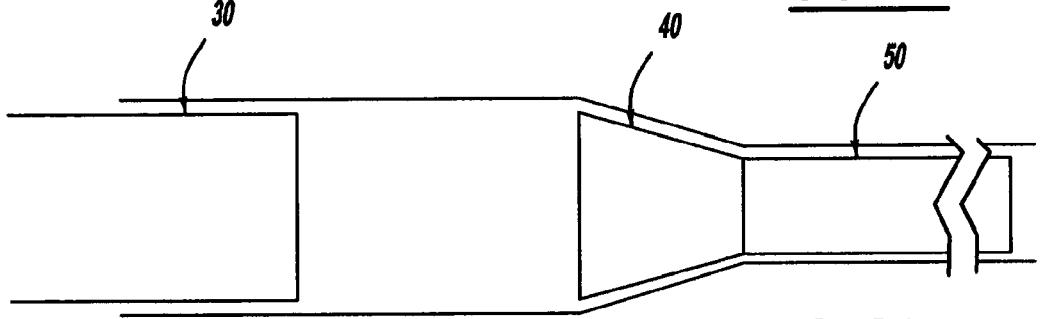
Figure 6F:
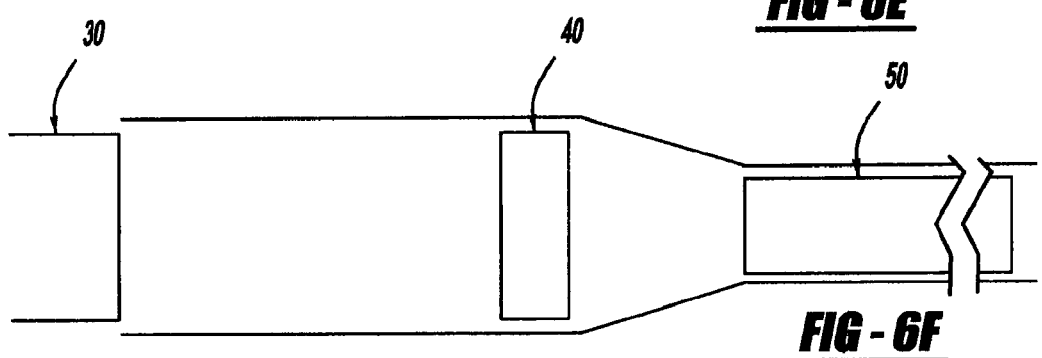

To further illustrate, top and side views, respectively, of the right hand side of FIG. 5a are given in FIGS. 5f and 5g. They show the oval isoareal shape 500 disposed between two circular die shapes 400 and 600.

Sacrificial Puck

In a preferred embodiment, a so-called sacrificial puck is used to improve the efficiency of the extrusion process. The concept of using a sacrificial puck is illustrated in FIG. 6; its use is readily adapted to other configurations. In referring to FIG. 6, a ram 30 is provided in a retracted position with respect to the deformation chamber 2. FIG. 3b shows the ram 30 retracted and the deformation chamber 2 filled with a rod-like bulk material 50 and a sacrificial puck 40. The sacrificial puck 40 is preferably made of a crosslinked polymer, which may be the same as the crosslinked polymer of the bulk material 50. It is preferably of approximately the same cross-sectional shape and area as the bulk material 50 to be extruded. In FIG. 3c, the ram 30 is shown pushing on the sacrificial puck 40, which in turn pushes on the bulk material 50 to move the bulk material 50 through the reducing die 6 into the cooling chamber 4. FIG. 3d shows the situation at the end of the stroke of the ram 30. The bulk material 50 is sitting completely in the cooling chamber 4, while the sacrificial puck 30 occupies the reducing die 6. Upon retraction of the ram 30 as shown in FIG. 3e, the sacrificial puck 40 tends to return to its original dimension because it is not being cooled in the cooling chamber as the bulk material 50 is. As a result, the sacrificial puck tends to extricate itself from the reducing die as shown in FIG. 3f. The sacrificial puck 40 can then be removed from the deformation chamber and the process repeated after a cycle time in which the bulk material 50 cools to a suitable solidification temperature as discussed above.

Rollers

In various embodiments, working of bulk material according to the invention is provided by passing the bulk material between sets of rollers, while applying force to the bulk material by means of the rollers to change a dimension of the material in the transverse direction. The geometry of a roller system is illustrated in a simple system in FIG. 7. FIG. 7a shows a perspective view of a bulk material in the shape of a cylinder as it is passed between rollers 100. The view of FIG. 7b is down the axial direction of the bulk material 50. Pressure is applied to the rollers as indicated by the arrows in FIG. 7b to change the dimension from $d_1$ to $d_2$, as illustrated in FIG. 7c. It is seen from FIG. 7 that one distinction between applying force by rollers and applying force by extruding is that when rollers are used, the force tends to be applied in a finite number of points around the bulk material, whereas for the extruding embodiment, force tends to be applied all around the cross-section of the bulk material.

As is well known, the rollers 100 normally have roller or other means for advancing the bulk material 50, while passing the material between rollers that provide pinch points or restrictions. Working of the material is accomplished in some embodiments by passing the material between a single set of rollers. If desired, additional working can be accomplished with a single set of rollers by rolling the material back and forth between the rollers, and/or by passing the material between the rollers more than once.

Figure 8:
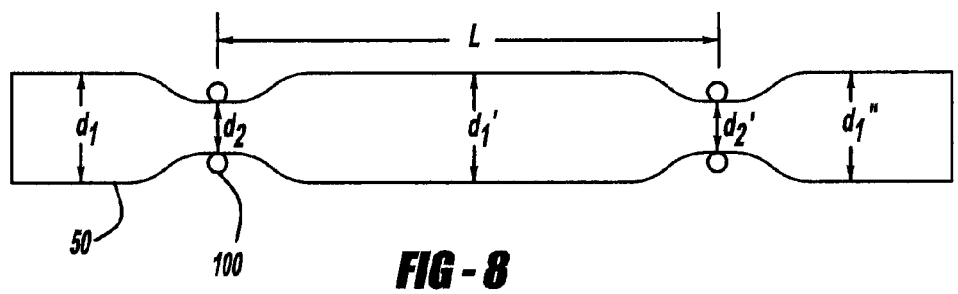

In various embodiments the rollers are spaced sufficiently far apart and the velocity of the rollers is selected to provide restriction points far enough apart that the compressed dimension of the material after passing through the first rollers recovers at least in part before being recompressed with a second set of rollers. This is illustrated in FIG. 8. As with extrusion through a series of decreasing and increasing dies, the original dimension $d_1$ is reduced to $d_2$ and recovers to $d_1'$ after the first set of rollers. The second set of rollers compresses the dimension to $d_2'$, while after the second rollers the dimension increases to $d_1''$, which is about the same as $d_1$. If the distance L between the first and last set of rollers is shorter than the total length of the material worked, the multiple rollers showed in non-limiting fashion in FIG. 8 can be set up or programmed to reverse to provide a back and forth movement of the material between the rollers. In this way, a desired amount of working can be applied in a mechanically convenient way. As before, the dimension of the material tends to recover once the pressure applied by the rollers is relieved.

In various embodiments, a series of rollers is provided close enough together that the dimension of the material does not fully recover in the time it takes the material to travel between the individual pairs of rollers in the series. In this way a series of rollers is used to provide pressure along a relatively long section of the bulk material 50 as it is transported by the motion of the rollers. Such a situation is illustrated by FIG. 7a, in a non-limiting configuration.

Whatever the spacing of the rollers, in various embodiments the individual sets of rollers are provided with offset configurations. For example, a first set of rollers is provided in a first orientation as illustrated in non-limiting fashion in FIG. 7b. A second set of rollers is provided in a second orientation, for example according to the illustration in FIG. 7d. Thus FIG. 7c represents deformation in a first transverse direction to decrease the dimension to $d_2$, while FIG. 7d represents deformation in a second transverse direction. In this further way, the material can be worked to a desired extent to accomplish a reduction in the free radical concentration induced in the material by the crosslinking step.

Other configurations of rollers are possible based on the description here. The unifying aspect is that the rollers provide constrictions or pinch points that change the dimension of the material being worked in order to induce a desired amount of material flow. It is also appreciated that not all the rollers in a system need be drive rollers. Rather, one of more of the rollers can be configured to provide movement to the material, while the others can be configured to provide compression only.

In various embodiments, the material is treated with rollers while being maintained at a compression deformable temperature, for example in a constant temperature oven. In other embodiments, the working of the material by rollers occurs in ambient conditions to permit the material to cool at the same time it is being worked. As desired, the pressure of the rollers applied over time can be varied, for example to slowly reduce the pressure applied (and thus the dimension change induced in the transverse direction) until the material has reached a solidification temperature.

Figure 7F:
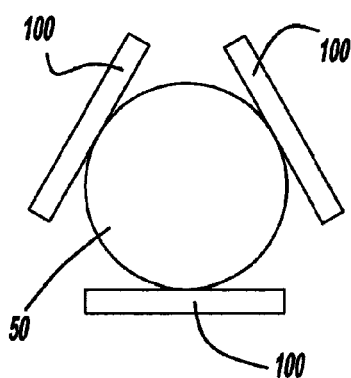
FIGS. 7 and 8 illustrate working the material using rollers.
Figure 7G:
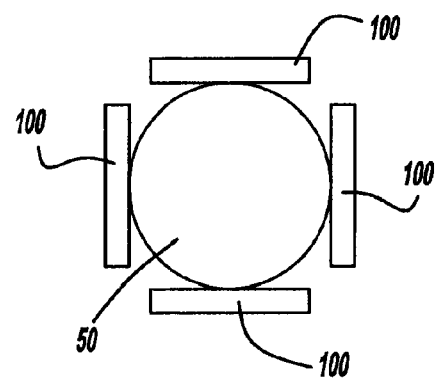

In general, the rollers are configured to provide a desired pressure regime about the cross-sectional area of the bulk material. For example, a 2-roller system is illustrated in FIG. 7a, while 3-roller systems are illustrated in FIG. 7f, and 4-roller systems are illustrated in FIG. 7g.

The amount of working is also varied in various embodiments by providing roller means with varying speeds. The time that the bulk material spends in a compressed state due to the action of the rollers is inversely proportional to the speed by which the rollers move the bulk material through the apparatus.

Pressure is applied by the roller systems by known mechanical means, such as without limitation gears, hydraulics, springs, and the like. A compression ratio can be defined that is analogous to the draw ratio defined for extrusion. Referring to FIG. 7, the compression ratio is defined by the ratio of the original dimension $d_1$ to the compressed dimension $d_2$. In various embodiments, preferred values for the restriction ratio take on the same values as the draw ratio for the extrusion embodiment.

Compression Molding

Figure 9A:
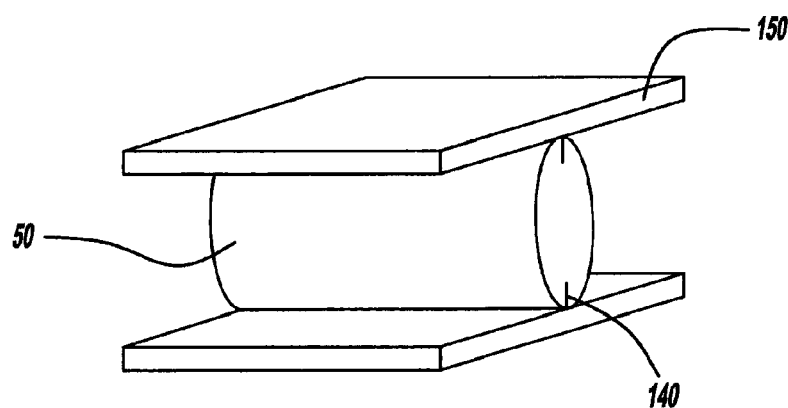
FIG. 9 shows compression methods of changing the dimensions of the material.
Figure 9B:
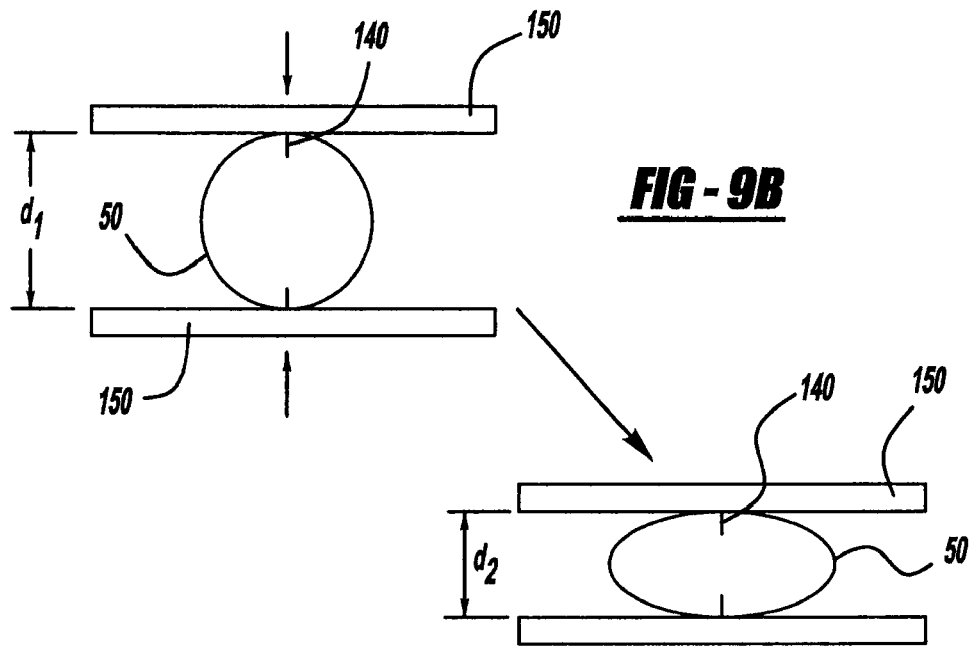
Figure 9C:
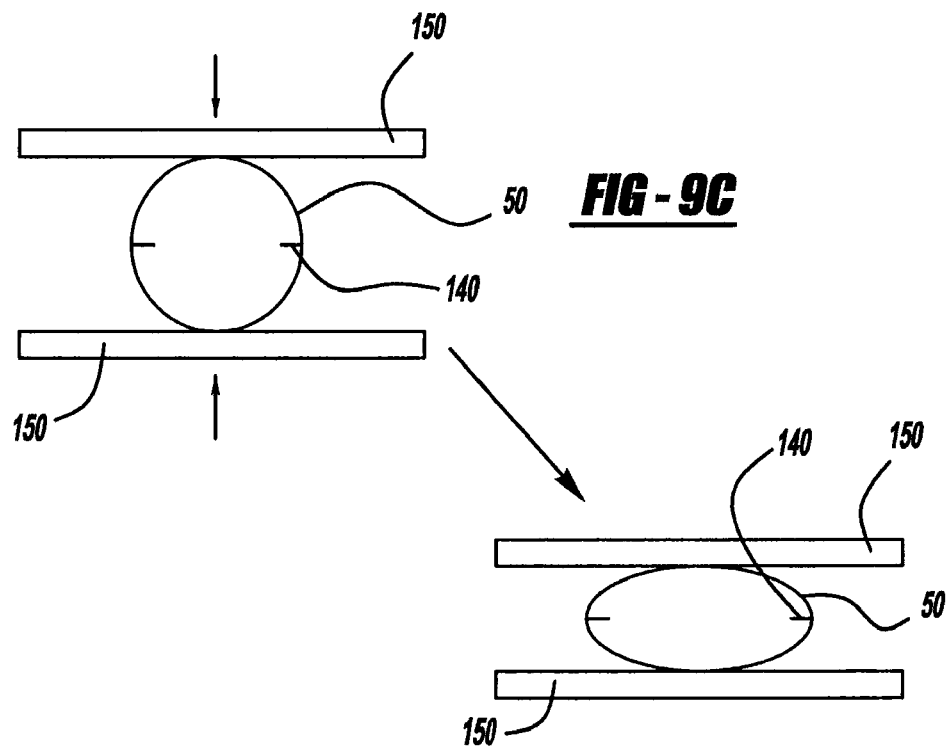

Another way of working the material by changing a dimension in the transverse direction is to apply pressure between plates in a compression molding fashion. The process is illustrated in a non-limiting way in FIG. 9. FIG. 9a shows a perspective drawing of an elongate bulk material 50 between the plates 150 of a compression molding apparatus. Tick marks 140 show the relative orientation of the bar 50 between the plates 150. FIG. 9b shows, in cross sectional view looking down the axial direction of the bulk material (show for illustration as a cylinder with circular section), the plates 150 in contact with the material before and after reduction of the transverse dimension from $d_1$ to $d_2$. A compression ratio is defined as $d_1/d_2$, which in various embodiments takes on preferred values such as those given above for draw ratio in the extrusion case. After compression, the pressure is optionally relieved (not shown) and the material is cooled. Alternatively, the material 50 is subjected to a series of compressions to provide a desired amount of working of the bulk material. Subsequent compressions can take place with the material in the same orientation as for the first compression. In various embodiments, subsequent compressions are made with the material in a different orientation with respect to the plates. As illustrated by FIG. 9c in a non-limiting fashion, the material is turned 90° from its first orientation, and compression force is again applied. In various embodiments, the process of compression and pressure relief is repeated using various orientations to achieve a desired amount of working of the bulk material.

FIG. 9 shows the compressive plates oriented parallel to one another, so that compression occurs to an equal extent all along the bulk material. The compressive method, however, is completely general, allowing for compression between plates that are tilted relative to each other, so as to provide an unequal compression ratio along the bulk material. After relieving the compression pressure, subsequent compressions can be carried out in the same or different configuration to provide the desired amount of "working" and material flow throughout the treated bulk material. In one embodiment, the orientation of the plates during contact with the bulk material is changed during contact to provide a kind of rolling massage along the length of the axial direction of the bulk material. In various embodiments, at least one of the plates 150 is provided with a curvature so that a rolling contact is maintained between the bulk material and two curved plates or a flat plate and a curved plate. It is readily seen that embodiments with curved plates in arrangements like FIG. 9 have many features in common with the process of applying pressure with rollers described above.

The methods described herein—extrusion, treatment by rollers, and compression molding, by way of non-limiting example—all involve the application of pressure to a bulk material in such a way that a dimension in the transverse direction of the bulk material is changed from its original value. As a result of the pressure application, material in the bulk material flows so that the bulk material takes on a different shape. In many cases, pressure is applied in the transverse direction to change the dimension. In the case of the increasing die, pressure or back pressure is applied in the axial direction to provide for the material flow. However it is applied, when the pressure is then reduced or relieved, the bulk material tends to undergo a recovery in dimensions back to approximately the starting value, due to the crosslinked nature of the bulk material on which the pressure is being applied. Both processes—compression and pressure relief—cause material to flow and the bulk material to be "worked". It is believed that the material flow leads to quenching of free radicals and/or the sequestering of free radicals in local environments in the bulk material where they are not susceptible to reaction with adventitious oxygen, water, or other oxidizing chemicals.

In various embodiments, the methods call for sequential pressuring and relief of pressure to produce a working or kneading of the material. Alternatively, the methods provide for a single compression and a single pressure relief step. When the pressure is relieved and the temperature is still above the solidification temperature (see below), the dimension reduced by application of pressure tends to recover to approximately its original value. In some embodiments, the cross sectional area of the elongated bulk material changes (decreases or increases) in response to the applied pressure; upon relief, the cross sectional area tends to return to approximately its original value. In other embodiments, the cross sectional area essentially does not change (examples are the isoareal dies, compression between rollers, and compression between plates) but at least one dimension in the transverse direction is decreased; upon relief, the dimensions tend to return to their original values and the shape to the original shape.

Cooling

After crosslinking, heating to a compression deformable temperature, and working as described above, in various embodiments the polymeric material is cooled before further processing. Alternatively, the extruded bulk material can be directly processed by the stress relief step described below. In a non-limiting embodiment, the rod or other bulk material characterized by an axial direction is cooled to a solidification temperature in a cooling chamber or other means while pressure is maintained sufficient to keep the dimension of the extruded bulk material below the original dimension of the crosslinked bulk material. In the extrusion or other compressive force embodiments, the pressure required to maintain the dimension lower than the original dimension may be more or less pressure than required to originally change the shape of the polymer, such as through extrusion. As noted, the bulk material such as extruded UHMWPE is held in a cooling chamber or similar device for a sufficient time to reach a temperature at which the bulk material no longer has a tendency to increase in dimension upon removal of the pressure. This temperature is designated as the solidification temperature; for UHMWPE the solidification temperature is reached when a thermostat embedded in the cooling wall (about 1 mm from the inside wall surface) reads about 30° C. The solidification temperature is not a phase change temperature such as a melting or freezing. It is also to be noted that a material such as UHMWPE can be cooled to the solidification temperature independently of whether the material was heated above or below the melting point in a previous processing step.

In various embodiments, after extrusion or other application of deforming force in a direction orthogonal to the axial direction of the crosslinked polymeric bulk material, the compressive deforming force is maintained on the bulk material until the bulk material cools to the solidification temperature. Such a maintenance of compressive force is conveniently provided in the reducing die embodiment illustrated in FIGS. 1 and 2. After extrusion through the reducing die 6, the bulk material is held in the cooling chamber 4. In the embodiment shown in the Figures, the cooling chamber is of such a size and shape as to hold the extruded bulk material at a dimension or diameter $d_3$, which is less than the original dimension $d_1$ of the bulk material and is conveniently about the same as the extruded dimension $d_2$ in a non-limiting example. The crosslinked material has a tendency to return to its original dimension by expanding when the temperature is above the solidification temperature. The expansion force of the bulk material is counteracted by the walls of the cooling chamber, with the result that compressive force is maintained on the bulk material while it cools. In various embodiments, the cooling chamber is provided with cooling means such as cooling jackets or coils to remove heat from the cooling chamber and the extruded polymer bulk material.

Referring to the figures for illustration, as the polymeric extruded bulk material cools in the cooling chamber, a temperature is reached at which the material no longer has a tendency to expand or revert to its original dimension $d_1$. At this temperature, called the solidification temperature, the bulk material no longer exerts pressure on the walls of the cooling chamber and can be removed. In preferred embodiments, the material is cooled to about 30° C., as measured by thermostats in the walls of the chamber, before removal.

The temperatures of the deformation chamber and the cooling chamber can be measured by conventional means, such as by thermocouples embedded into the walls of the respective chambers. For example, it has been found that when a thermocouple in the wall of the cooling chamber indicates a temperature of 30° C., an extruded bulk material made of UHMWPE has reached a bulk temperature below a solidification temperature at which the material loses it tendency to expand. The temperature as measured with, for example, a thermocouple embedded in the wall of the cooling chamber does not necessarily represent a bulk or equilibrium temperature of the material in the cooling chamber. An appropriate rate of cooling may be provided in the cooling chamber by use of heat exchange fluids such as water or water glycol mixture, and the bulk material held in the cooling chamber for a time and until a temperature is reached at which it is observed that removal of the bulk material from the chamber does not result in significant increase in diameter. Thus, in various embodiments, cooling to a solidification temperature of, for example, 90° F. or 30° C. means leaving the extruded bulk material in the cooling chamber until the thermocouple embedded in the walls of the cooling chamber reads 90° F. or 30° C. As noted, it has been found that such a cooling period suffices for removal of the bulk material, even though the bulk equilibrium temperature of the interior of the bulk material could be higher than the measured temperature.

In various embodiments, the extruded bulk material is held in the cooling chamber for an additional period of time, such as 10 minutes, after the embedded thermocouple reads 90° F. or 30° C. The additional cooling period can enable the cooled material to be more easily removed from the cooling chamber. In one embodiment, when the thermocouple reaches a reading of 30° C., a programmable logic controller (plc) starts a timer that in turns gives a signal when the desired time has passed. At that time an operator can remove the compression deformed crosslinked material from the chamber, or rams or other suitable devices can be actuated to effect removal.

Alternatively, the compression deformed and worked material is allowed to cool without applied pressure. The workpiece tends to return to the original dimensions it had before the working. In various embodiments, the piece is extruded into air or into a cooling chamber of dimension approximately equal to that of the original workpiece. If rollers are used to compress and work the material, the roller tension can be removed and the material allowed to cool.

Stress Relieving

As noted above, after pressure is reduced or relieved in the working of the bulk materials, the dimensions of the bulk materials tend to return to approximately their original values. This is consistent with a certain amount of "shape memory" that is characteristic of crosslinked polymeric materials. Usually, however, the return to original dimensions is not 100%; under various models this is ascribable to incomplete return to an original equilibrium condition, to lack of an equilibrium condition in the first place, or even to a series of small irreversible changes in structure as a result of the working. Up to a certain point, such non-equilibrium conditions can be avoided or mitigated by operating at suitably low levels of draw ratio or compression ratio in the working steps described herein. But to a certain extent, some such small deviations from equilibrium are unavoidable. As a result, the worked and cooled material contains a certain amount of internal stress. Such stress is subject to relief over time when held at physiological conditions, which could lead to dimension changes and the like of the installed implant. This would be of course undesirable.

For at least these reasons, the bulk material is preferably stress relieved following working of the material in the transverse direction and optional cooling to a solidification temperature, and prior to being machined into a bearing component for use in a medical implant such as an artificial joint. In one embodiment, stress relieving is carried out by heating to a stress relief temperature, preferably below the melting point of the polymeric bulk material. If the cooling in the previous step is carried out while maintaining deformation force, the bulk material on stress relieving tends to expand and return to a dimension close to its original dimension. In the non-limiting example of an extruded rod, as the bulk material is heated, the diameter $d_3$ of the rod tends to increase to a diameter approaching $d_1$ of the original bulk material. In various non-limiting embodiments, it has been observed that the bulk material retains about 90-95% of its original dimension upon stress relieving or stress relief heating.

Stress relief is carried out in a variety of ways. In various embodiments, the bulk material is heated in an oven, is heated by infrared radiation, is subject to microwave radiation, or is treated with ultrasonic energy. In various aspects, the methods tend to increase the temperature of the bulk material and provide a thermal defect. However, it is believed that some of the methods, for example ultrasound, provide various energy other than thermal energy to provide for the stress relieving.

For thermal-based stress relieving, the stress relief process tends to run faster and more efficiently at higher temperatures. Accordingly, stress relief temperatures close to but less than the melting temperature are preferred, for example from the melting point to the melting point minus 30 or 40° C. For UHMWPE, preferred stress relief temperatures include in the range of about 100° C. to about 135° C., 110° C. to about 135° C., 120° C. to 135° C., and preferably 125° C. to about 135° C.

Stress relieving is carried out for a time to complete the stress relief process. In various embodiments, suitable times range from a few minutes to a few hours. Non-limiting examples include 1 to 12 hours, 2 to 10 hours, and 2 to 6 hours in an oven or other suitable means for maintaining a stress relief temperature. Although the stress relieving can be carried out in a vacuum, in an inert atmosphere, or in a package designed to exclude an atmosphere, it is preferably carried out in an air atmosphere.

Under some conditions, the solidified extruded bulk form exhibits a tendency to bend or otherwise deviate from a preferred straight or linear orientation during the heating or other treatment associated with stress relieving. To counter this tendency, in one embodiment, the bulk material is held in a mechanical device that functions to keep the bulk material straight (measured on the axial direction) during the stress relieving step. In a non-limiting example, the bulk material is placed into V-channels to keep it straight. For example, several V-channels are equally spaced from each other and are part of the same physical structure. The several V-channels may, for example, be welded to the structure at equal spacings. The extruded bars are positioned on a bottom set of V-channels and then another set of V-channels is set on top of the extruded bars to rest on top of the bars. These channels help to keep the bars straight during stress relieving.

In various embodiments, the product of the crosslinking, heating, compressing (working), cooling, and stress relieving steps is a bulk material having dimensions approximately equal to the original bulk material before crosslinking. As a result of the steps taken on the bulk material, the bulk material exhibits high tensile strength in the axial direction, a low but detectable level of free radical concentration, and a high degree of resistance to oxidation.

The process described can be followed with regard to the dimensions of the crosslinked polymer at various stages of the process. In various embodiments, a bulk material having an original dimension or diameter of $d_1$ is crosslinked and heated to a compression deformation temperature. The crosslinked heated material is then compressed to a dimension or diameter $d_2$ which is less than $d_1$. In an optional step, the material is then held while cooling at a diameter $d_3$ that may be the same as $d_2$, but in any case is less than the original dimension or diameter $d_1$. After cooling, stress relieving returns the bulk material to a diameter $d_4$ which is greater than $d_3$ and in some embodiments is approximately equal to the original dimension or diameter $d_1$. For example, if the original bulk material is a 3"×14" cylinder of UHMWPE, the treated preform resulting from the steps above preferably typically has a diameter of about 2.7 to 3 inches.

Following the treatment steps described above, the bulk material characterized by an axial direction is machined according to known methods to provide bearing components for implants. In the case of a cylindrical treated bulk material perform, it is preferred first to turn the outer diameter of the cylinder to remove any oxidized outer layers and to provide a straight and round cylinder for further processing. In a preferred embodiment, the cylinder is then cut into billets along the axial direction, and each billet is machined into a suitable bearing component. Preferably, the bearing components are machined from the billets in such a way that the in vivo load bearing axis of the bearing component corresponds to the axial direction of the bulk preform from which it is machined. Machining this way takes advantage of the increased tensile strength and other physical properties in the axial direction of the preform.

For example, in bearing components for joint replacements, the stresses at the bearing surface are typically multi-axial, and the magnitude of the stresses further depends on the conformity of the joint. For hip applications, the polar axis of the cup is aligned with the longitudinal axis of the extruded rod, corresponding to the axial direction. The wall of the cup, at the equator and rim, is parallel to the long axis of the rod, and will benefit from the enhanced strength in this direction during eccentric and rim loading scenarios.

Oxidative Resistance

It has been found that UHMWPE preforms, and bearing components made according to the invention have a high level of oxidative resistance, even though free radicals can be detected in the bulk material. To measure and quantify oxidative resistance of polymeric materials, it is common in the art to determine an oxidation index by infrared methods such as those based on ASTM F 2102-01. In the ASTM method, an oxidation peak area is integrated below the carbonyl peak between 1650 $cm^{-1}$ and 1850 $cm^{-1}$. The oxidation peak area is then normalized using the integrated area below the methane stretch between 1330 $cm^{-1}$ and 1396 $cm^{-1}$. Oxidation index is calculated by dividing the oxidation peak area by the normalization peak area. The normalization peak area accounts for variations due to the thickness of the sample and the like. Oxidative stability can then be expressed by a change in oxidation index upon accelerated aging. Alternatively, stability can be expressed as the value of oxidation attained after a certain exposure, since the oxidation index at the beginning of exposure is close to zero. In various embodiments, the oxidation index of crosslinked polymers of the invention changes by less than 0.5 after exposure at 70° C. to five atmospheres oxygen for four days. In preferred embodiments, the oxidation index shows a change of 0.2 or less, or shows essentially no change upon exposure to five atmospheres oxygen for four days. In a non-limiting example, the oxidation index reaches a value no higher than 1.0, preferably no higher than about 0.5, after two weeks of exposure to 5 atm oxygen at 70° C. In a preferred embodiment, the oxidation index attains a value no higher than 0.2 after two or after four weeks exposure at 70° to 5 atm oxygen, and preferably no higher than 0.1. In a particularly preferred embodiment, the specimen shows essentially no oxidation in the infrared spectrum (i.e. no development of carbonyl bands) during a two week or four week exposure. In interpreting the oxidative stability of UHMWPE prepared by these methods, it is to be kept in mind that the background noise or starting value in the oxidation index determination is sometimes on the order of 0.1 or 0.2, which may reflect background noise or a slight amount of oxidation in the starting material.

Oxidation stability such as discussed above is achieved in various embodiments despite the presence of a detectable level of free radicals in the crosslinked polymeric material. In various embodiments, the free radical concentration is above the ESR detection limit of about $0.06 \times 10^{15}$ spins/g and is less than that in a gamma sterilized UHMWPE that is not subject to any subsequent heat treatment (after sterilization) to reduce the free radical concentration. In various embodiments, the free radical concentration is less that $3 \times 10^{15}$, preferably less $1.5 \times 10^{15}$, and more preferably less than $1.0 \times 10^{15}$ spins/g. In various embodiments, the oxidation stability is comparable to that of melt processed UHMWPE, even if according to the invention the UHMWPE is processed only below the melting point.

Although the invention is not to be limited by theory, the free radicals in the deformation processed UHMWPE described above may be highly stabilized and inherently resistant to oxidative degradation. Alternatively or in addition, they may be trapped within crystalline regions of the bulk material and as a consequence may be unavailable to participate in the oxidation process. Because of the oxidation stability of the material, in various embodiments it is justifiable to employ gas permeable packaging and gas plasma sterilization for the processed radiation UHMWPE. This has the advantage of avoiding gamma sterilization, which would tend to increase the free radical concentration and lead to lower oxidation stability.

In various embodiments, the solid state deformation process provides polymers that are characterized by a crystal and molecular orientation. By molecular orientation is meant that polymer chains are oriented perpendicular to the direction of compression. By crystalline orientation it is meant that crystal planes in polyethylene, such as the 200 plane and the 110 plane are oriented to the direction parallel to the compression plane. In this way the crystal planes are oriented. The presence of the orientations can be shown by means of birefringent measurements, infrared spectra, and x-ray diffraction.

The plane of compression for articles compressed in a radial direction is understood to be a surface surrounding and parallel to the radial surface of the bulk material that is processed according to the invention. In the non-limiting example of a cylindrical rod, a sequence of circular cross sections along the axial direction defines a radial surface and a compression plane perpendicular to that surface. In response to compression around the radial plane, polymer chains orient themselves perpendicular to the direction of compression. This has the effect in a cylinder of providing molecular orientation generally parallel to the radial plane. It is believed that with this molecular and crystal orientation contributes to the enhancement of mechanical properties, and to anisotropy in the mechanical properties with respect to the axial and transverse (or radial) directions.

In various embodiments, crosslinked UHMWPE are provided that exhibit a high level of tensile strength in at least one direction. Advantageously, bearing components and implants are provided that take advantage of the increased strength of the bearing material. For example, in crosslinked UHMWPE, it is possible to achieve a tensile strength at break of at least 50 MPa, preferably at least 55 MPa, and more preferably at least 60 MPa. In various embodiments, materials are provided with a tensile strength at break in the range of 50-100 MPa, 55-100 MPa, 60-100 MPa, 50-90 MPa, 50-80 MPa, 50-70 MPa, 55-90 MPa, 55-80 MPa, 55-70 MPa, 60-90 MPa, 60-80 MPa, and 60-70 MPa. In a non-limiting embodiment the tensile strength of a UHMWPE prepared according the invention is about 64 MPa in the axial direction.

Embodiments of the present invention are further illustrated through the following non-limiting examples.

EXAMPLES

Comparative Example

Isostatically molded UHMWPE bar stock (Ticona, Inc., Bishop, Tex.) is packaged in an argon environment and gamma sterilized to a dose of 25 to 40 kGy

Example 1

Radiation crosslinked, deformation processed UHMWPE is produced using the following steps:

1. Radiation crosslinking. Isostatically molded UHMWPE rods of dimensions 3"×14" (GUR resin from Ticona, Inc., Bishop, Tex. fully consolidated according to the isostatic pressure steps described in U.S. Pat. No. 5,688,453) are vacuum packed in a foilized bag and gamma radiation crosslinked with a nominal dose of 50 kGy.

2. Preheating. Prior to deformation processing, the rod is removed from the foilized bag and raised to 133° C. for 4 to 12 hours in an oven.

3. Solid state, hydrostatic extrusion. The heated rod is then removed from the oven and placed in the holding chamber of a press. The temperature of the holding chamber is 130° C.±5° C. The bar is then ram extruded using a sacrificial puck made of crosslinked UHMWPE through a circular die, into a cooling chamber with a diametral compression ratio of 1.5 (diameter of 3" down to 2").

4. Cooling and solidification. The cooling chamber is sized so as to maintain the extruded rod in a deformed state. The walls of the cooling chamber are water-cooled. When thermocouples embedded in the wall (about 1 mm from the inside wall) read 30° C., the solidified rod is removed, optionally after an additional cooling period of ten minutes, in a non-limiting example. If desired, a second bar is ram extruded to eject the cooled bar from the cooling chamber, once the temperature reaches about 30° C.

5. Stress relief, annealing. The deformed rod is then heated at 133±2° C. for 5 hours. The annealing also improves dimensional stability in the material. The rod is then slowly cooled to room temperature. The extruded rod retains about 90-95% of its initial diameter after the stress relief step.

6. Gas plasma sterilization. After cooling, a liner or other bearing material is machined and the machined part is non-irradiatively sterilized (e.g., with ethylene oxide or gas plasma)

Specimen Preparation and Orientation

For compression tests and accelerated aging, right rectangular prism specimens are evaluated. The specimens measure 12.7 mm by 12.7 mm by 25.4 mm (0.50 in. by 0.50 in. by 1.00 in.) They are machined from the rod stock parallel (the axial direction) or perpendicular (the transverse direction) to the long axis.

For tensile tests, dumbbell-shaped tensile specimens consistent with the Type IV and V specimen description provided in ASTM D638-02 a are tested. Specimens are 3.2±0.1 mm thick. Specimens are oriented parallel or perpendicular to the long axis, reflecting the axial and transverse directions, respectively).

Physical and Mechanical Properties

Tensile strength at break is determined according to ASTM 638-02a.

The concentration of free radicals in the UHMWPE materials is characterized using an ESR spectrometer (Bruker EMX), as described previously in Jahan et al., J. Biomedical Materials Research, 1991; Vol. 25, pp 1005-1017. The spectrometer operates at 9.8 GHz (X Band) microwave frequency and 100 kHz modulation/detection frequency, and is fitted with a high sensitivity resonator cavity. For a good spectral resolution and/or signal-to-noise ratio, modulation amplitude is varied between 0.5 and 5.0 Gauss, and microwave power between 0.5 and 2.0 mW.

Accelerated Aging

Specimens are aged in 5 atmospheres of oxygen in accordance with ASTM F 2003-00. Some specimens are aged for two weeks according to this standard, and others are aged for four weeks. Aging is performed in a stainless steel pressure vessel. The specimens are chosen and oriented such that the tested axis is vertical. Thus, the top and bottom faces are perpendicular to the test axis. The top face is labeled for later identification. The vessels are then filled with oxygen and purged five times to ensure the purity of the aging environment. The prisms rest on a flat surface inside the pressure vessel; thus each prism's bottom face is not exposed to oxygen, but each of its other faces are exposed to oxygen throughout the aging period.

The vessel is placed in the oven at room temperature (24±2° C.), and the oven was heated to the aging temperature of 70.0±0.1° C. at a rate of 0.1° C./min.

FTIR Analysis

Materials are evaluated before and after accelerated aging by Fourier transform infrared spectroscopy (FTIR) in transmission (Excalibur series FTS3000 with a UMA-500 microscope attachment; Bio-Rad Laboratories, Hercules, Calif.). FTIR profiling is conducted perpendicular to the transverse direction.

Oxidation index measurement and calculations are based on ASTM F 2102-01. Oxidation peak area is the integrated area below the carbonyl peak between 1650 and 1850 $cm^{-1}$. The normalization peak area is the integrated area below the methylene stretch between 1330 and 1396 $cm^{-1}$. Oxidation index is calculated by dividing the oxidation peak area by the normalization peak area.

Data for the Comparative Example and Example 1 are given in the Table

|  | Comparative Example | Example 1 | Example 1, axial | Example 1, transverse |
|---|---|---|---|---|
| Tensile Strength at Break [MPa] | 46.8 ± 2.0 |  | 64.7 ± 4.5 | 46.1 ± 3.5 |

-continued

|  | Comparative Example | Example 1 | Example 1, axial | Example 1, transverse |
|---|---|---|---|---|
| Free radical concentration, spins/g | $3.82 \times 10^{15}$ | $0.22 \times 10^{15}$ | | |
| Oxidation index before aging (at surface) | 0.2 | <0.1 | | |
| Oxidation index after aging (at surface) | 1.2 | <0.1 | | |

Example 2

Isoareal Restriction

A bulk UHMWPE in the form of a 3"×14" cylinder is subject to 5 Mrad of gamma irradiation to crosslink it. The crosslinked bar is preheated to 130° C. for 4 hours. The bar is then extruded through a constant area elliptical mold tool. The cross-sectional area is maintained about 7 sq. in., which is the cross-sectional diameter of the bar. Inside the elliptical mold tool, the shape starts at a 3 inch diameter circle and changes into an ellipse (1.5 in. minor axis×6 in. major axis) at a position 0.75 inches from the start. The tool changes back to 3 inch diameter circle at position 1.5 inches from the start. Then the tool changes to an ellipse (1.5 inch minor×6 inch major axis) at position 2.25 inches from the start. The second ellipse is oriented 90° to the first ellipse. Then the tool changes back to a 3 inch diameter circle at a position 3 inches from the start. The bulk material is extruded from the elliptical material mold tool where it is cooled. During cooling, the bars change shape from a 3 inch diameter to a rounded off rectangular shape. A stress relief cycle is carried out by heating to 130° C. for 4 hours. After heating for 4 hours, the bar is slowly cooled. After stress relief, the bars maintain a rounded off rectangular shape.

The tensile strength of the bar in the axial direction is about 8000 psi (about 55.2 MPa) while the impact strength in the transverse direction is about 70-75 kJ/m². The free radical concentration measured by epr is about $2.6 \times 10^{14}$ spins/g (or $0.26 \times 10^{15}$ spins/g).

The examples and other embodiments described herein are exemplary and not intended to be limiting in describing the full scope of compositions and methods of this invention. Equivalent changes, modifications and variations of specific embodiments, materials, compositions and methods may be made with substantially similar results.

We claim:

1. A method of processing a crosslinked ultra high molecular weight polyethylene (UHMWPE), wherein the UHMWPE is characterized by a dimension $d_1$ in a direction orthogonal to an axial direction, the method comprising:
    heating the crosslinked UHMWPE to a compression deformable temperature below the crystalline melting point of the UHMWPE;
    applying pressure on the UHMWPE to reduce the dimension to a value $d_2$ less than $d_1$;
    cooling the crosslinked UHMWPE to a solidification temperature;
    stress relieving the cooled crosslinked UHMWPE to make an oriented UHMWPE molded article having a tensile strength measured in the axial direction that is 20% or more higher than the tensile strength measured in the orthogonal direction; and then
    machining a load bearing medical implant component from the cooled UHMWPE, wherein the component has a load bearing axis substantially coincident with the axial direction of the crosslinked UHMWPE.

2. A method according to claim 1, comprising, after applying pressure and prior to cooling, releasing the pressure to permit at least a partial recovery of dimension $d_2$ to a dimension $d_1'$ greater than $d_2$ and reapplying the pressure to reduce the dimension to a value $d_2'$ less than $d_1'$.

3. A method according to claim 1, comprising applying pressure on the UHMWPE in a direction orthogonal to the axial direction.

4. A method according to claim 1, wherein the pressure is applied by extrusion through one or more dies.

5. A method according to claim 1, wherein the pressure is applied by rollers.

6. A method according to claim 1, wherein the pressure is applied by compression molding.

7. A method according to claim 1, wherein the pressure is applied by any combination of dies, rollers, and compression molding.

8. A method according to claim 1, wherein pressure is applied by extrusion through a die having a cross-sectional area less than the cross-sectional area of the crosslinked UHMWPE.

9. A method according to claim 1, wherein the crosslinked UHMWPE is in the form of a cylinder.

10. A method according to claim 9, wherein the cylinder has a circular cross-section perpendicular to the axial direction of the cylinder.

11. A method according to claim 1, wherein the crosslinked UHMWPE is crosslinked by gamma-irradiation at a dose of 1 to 100 MRad.

12. A method according to claim 1, comprising cooling the crosslinked UHMWPE while maintaining applied pressure.

13. A method according to claim 12, further comprising stress relieving the cooled UHMWPE before the machining step.

14. A method according to claim 13, wherein stress relieving comprises heating to a stress relief temperature below the melting point of the UHMWPE.

15. A method according to claim 13, wherein stress relieving comprises treating with ultrasonic energy.

16. A method according to claim 13, wherein stress relieving comprises heating with infrared radiation.

17. A method according to claim 13, wherein stress relieving comprises heating with microwave energy.

18. A method for reducing the free radical concentration in irradiated crosslinked bulk polymer and producing a medical implant bearing component from the polymer, the polymer being in the form of a bulk material elongated in an axial direction, the method comprising:
    heating the crosslinked bulk material to a compression deformable temperature;
    applying a force to deform the heated bulk material in a direction orthogonal to the axial direction; and
    cooling the polymer to a solidification temperature while maintaining deformation pressure;
    stress relieving the cooled polymer to make an oriented molded article having a tensile strength measured in the axial direction that is 20% or more higher than the tensile strength measured in the orthogonal direction; and machining a load bearing medical implant component from the cooled polymer, wherein the component has a load bearing axis that corresponds to the axial direction of the crosslinked polymer.

19. A method according to claim 18, wherein the crosslinked bulk material is crosslinked by gamma-irradiation.

20. A method according to claim 19, wherein the bulk polymer comprises UHMWPE.

21. A method according to claim 20, wherein the bulk polymer comprises a bar having a circular cross-section.

22. A method according to claim 21, wherein the circular cross-section has a diameter of from 2-4 inches.

23. A method according to claim 22, wherein the circular cross-section has a diameter of about 3 inches.

24. A method according to claim 18, comprising extruding the cross-linked bulk polymer through a decreasing die.

25. A method according to claim 18, comprising extruding the cross-linked bulk polymer through an increasing die.

26. A method according to claim 18, comprising extruding the cross-linked bulk polymer through an isoareal die.

27. A method according to claim 18, comprising multiple extrusions through a single die and/or extrusion through a plurality of dies.

28. A method according to claim 18, comprising applying deforming force with rollers.

29. A method according to claim 18 comprising applying deforming force by compression molding.

30. A method according to claim 18, wherein the compression deformable temperature is less than the crystalline melting point of the polymer.

31. A method according to claim 18, wherein stress relieving comprises heating to a stress relief temperature below the melting point of the UHMWPE.

32. A method according to claim 18, wherein stress relieving comprises treating with ultrasonic energy.

33. A method according to claim 18, wherein stress relieving comprises heating with infrared radiation.

34. A method according to claim 18, wherein stress relieving comprises heating with microwave energy 35. A method of processing a crosslinked ultra high molecular weight polyethylene (UHMWPE), wherein the UHMWPE is characterized by a dimension $d_1$ in a direction orthogonal to an axial direction, and further characterized by a cross-sectional area $A_1$ in a transverse section perpendicular to the axial direction, the method comprising:
  heating the crosslinked UHMWPE to a compression deformable temperature below the crystalline melting point;
  applying pressure on the UHMWPE in such a way as to increase the dimension to a value $d_2$ greater than $d_1$ and to increase the cross-sectional area to a value $A_2$ greater than $A_1$;
  relieving the pressure to permit a return to a value $d_1'$ approximately equal to $d_1$ and an areal value $A_1'$ approximately equal to $A_1$; and
  cooling the crosslinked UHMWPE to a solidification temperature.

36. A method according to claim 35, wherein the UHMWPE is crosslinked with gamma-irradiation.

37. A method according to claim 35, wherein pressure is applied by extruding through an increasing die.

* * * * *